(12) United States Patent
Fotsing

(10) Patent No.: US 10,412,986 B2
(45) Date of Patent: Sep. 17, 2019

(54) PROCESS FOR THE SYNTHESIS OF SUBSTITUTED 1-BENZYL-3-(1-(ISOXAZOL-4-YLMETHYL)-1H-PYRAZOL-4-YL)IMIDAZOLIDINE-2,4-DIONES

(71) Applicant: SENOMYX, INC., San Diego, CA (US)

(72) Inventor: Joseph R. Fotsing, San Diego, CA (US)

(73) Assignee: SENOMYX, INC., San Diego, CA (US)

( * ) Notice: Subject to any disclaimer, the term of this patent is extended or adjusted under 35 U.S.C. 154(b) by 0 days.

(21) Appl. No.: 15/948,282

(22) Filed: Apr. 9, 2018

(65) Prior Publication Data
US 2018/0220689 A1    Aug. 9, 2018

Related U.S. Application Data

(62) Division of application No. 14/619,458, filed on Feb. 11, 2015, now Pat. No. 9,936,723.

(60) Provisional application No. 61/938,861, filed on Feb. 12, 2014.

(51) Int. Cl.
| | |
|---|---|
| A23L 27/20 | (2016.01) |
| C07D 413/06 | (2006.01) |
| C07D 217/16 | (2006.01) |
| A23L 27/00 | (2016.01) |
| C07D 413/14 | (2006.01) |
| C07D 471/04 | (2006.01) |
| C07D 309/12 | (2006.01) |

(52) U.S. Cl.
CPC ....... *A23L 27/2054* (2016.08); *A23L 27/2056* (2016.08); *A23L 27/86* (2016.08); *C07D 217/16* (2013.01); *C07D 309/12* (2013.01); *C07D 413/06* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 5,112,598 A | 5/1992 | Biesalski et al. | |
| 5,556,611 A | 9/1996 | Biesalski et al. | |
| 5,698,155 A | 12/1997 | Grosswald et al. | |
| 7,105,650 B2 | 9/2006 | Adler et al. | |
| 7,338,771 B2 | 3/2008 | Pronin et al. | |
| 7,393,654 B2 | 7/2008 | Adler et al. | |
| 7,396,651 B2 | 7/2008 | Adler et al. | |
| 7,399,601 B2 | 7/2008 | Adler et al. | |
| 7,407,765 B2 | 8/2008 | Li et al. | |
| 7,517,972 B2 | 4/2009 | Adler et al. | |
| 7,638,289 B2 | 12/2009 | Adler et al. | |
| 7,704,698 B2 | 4/2010 | Adler et al. | |
| 7,718,383 B2 | 5/2010 | Adler et al. | |
| 7,723,051 B2 | 5/2010 | Adler et al. | |
| 7,723,481 B2 | 5/2010 | Adler et al. | |
| 7,736,862 B2 | 6/2010 | Adler et al. | |
| 7,776,561 B2 | 8/2010 | Pronin et al. | |
| 7,785,802 B2 | 8/2010 | Adler et al. | |
| 7,794,959 B2 | 9/2010 | Li et al. | |
| 7,811,788 B2 | 10/2010 | Li et al. | |
| 7,816,093 B2 | 10/2010 | Adler et al. | |
| 7,883,856 B2 | 2/2011 | Li et al. | |
| 7,915,003 B2 | 3/2011 | Li et al. | |

(Continued)

FOREIGN PATENT DOCUMENTS

| | | |
|---|---|---|
| CA | 2647316 | 11/2007 |
| WO | 2001/18050 | 3/2001 |

(Continued)

OTHER PUBLICATIONS

Adler et al., "A Novel Family of Mammalian Taste Receptors," Cell 100(6):693-702 (2000).

(Continued)

*Primary Examiner* — Kamal A Saeed
(74) *Attorney, Agent, or Firm* — Robin L. Teskin; LeClairRyan PLLC

(57) ABSTRACT

The present invention relates to processes and intermediates for the preparation of compounds of formula (I):

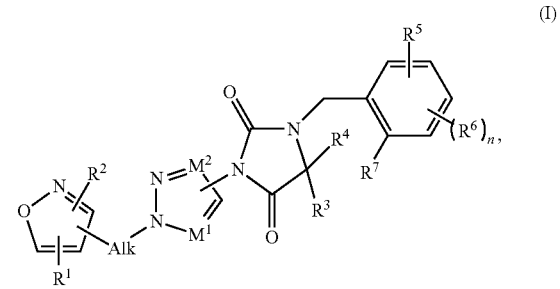

or a salt or oxide thereof wherein Alk, $M^1$, $M^2$, $R^1$, $R^2$, $R^3$, $R^4$, $R^5$, $R^6$, $R^7$, and n are as described herein.
The present invention also relates to compounds of formula (I) and composition comprising a compound of formula (I). Also disclosed is a method of altering or improving the taste of a composition that includes adding to the composition at least one compound of formula (I), in an amount effective to obtain a modified composition having altered or improved taste relative to an otherwise identical composition lacking said compound.

7 Claims, 4 Drawing Sheets

(56) References Cited

U.S. PATENT DOCUMENTS

| | | | |
|---|---|---|---|
| 7,927,823 B2 | 4/2011 | Adler et al. | |
| 7,932,056 B2 | 4/2011 | Moyer et al. | |
| 7,939,276 B2 | 5/2011 | Li et al. | |
| 7,939,671 B2 | 5/2011 | Li et al. | |
| 7,968,693 B2 | 6/2011 | Adler | |
| 8,017,751 B2 | 9/2011 | Adler et al. | |
| 8,030,008 B2 | 10/2011 | Li et al. | |
| 8,030,009 B2 | 10/2011 | Adler et al. | |
| 8,030,451 B2 | 10/2011 | Adler et al. | |
| 8,030,468 B2 | 10/2011 | Adler et al. | |
| 8,071,320 B2 | 12/2011 | Pronin et al. | |
| 8,076,491 B2 * | 12/2011 | Karanewsky | A61K 31/135 548/247 |
| 8,153,386 B2 | 4/2012 | Adler et al. | |
| 8,221,987 B2 | 7/2012 | Li et al. | |
| 8,273,542 B2 | 9/2012 | Li et al. | |
| 8,318,447 B2 | 11/2012 | Li et al. | |
| 8,338,115 B2 | 12/2012 | Adler et al. | |
| 8,445,692 B2 | 5/2013 | Karanewsky et al. | |
| 8,524,464 B2 | 9/2013 | Li et al. | |
| 2010/0254916 A1 | 10/2010 | Karanewsky et al. | |

FOREIGN PATENT DOCUMENTS

| | | |
|---|---|---|
| WO | 2001/77676 | 10/2001 |
| WO | 2006010643 | 2/2006 |
| WO | 2011/106114 | 1/2011 |

OTHER PUBLICATIONS

Anon., Sichere Chemiarb., 1984, 36, 143-144.

Blanco-Ania, D et al. "Synthesis of Tetrahydro-betta-carbolines and Tetrahydroisoquinolines Fused to Pyrrodlidines and Solution-Phase Parallel Acylation." Journal of Combinatorial Chemistry, vol. 11, 2009, pp. 536-546 [online], [retrieved on Apr. 16, 2015]. Retrieved from the Internet <URL: http://pubs.acs.org/doi/abs/10.1021/cc800191w>; p. 539, figure 1.

Chandrashekar et al., "T2Rs Function as Bitter Taste Receptors," Cell 100(6):703-711 (2000).

Greene, Protective Groups in Organic Synthesis, John Wiley & Sons, New York (1991).

Hayashi, K et al. Facile Preparation of optically pure (3S)- and (3R)-1,2,3,4-Tetrahydroisoquinoline-3-Carboxylic Acid. Chem. Pharm. Bull., vol. 31, No. 1, 1983, pp. 312-314 [online], [retrieved on Apr. 16, 2015]. Retrieved from the Internet <URL: https://www.thevespiary.org/library/Files_Uploaded_by_Users/no1uno/pdf/Medicinial/Analgetics/Morphinans/Precursor.Isoquinolines/Aysmmetric/Hayashi.etal.Facile.Preparation.ofOptically.Pure.1234.THIQ.3Carboxylic.Acid.pdf>, page, chart 1.

Iwata et al., "Taste Transducitons in Taste Receptor Cells: Basic Tastes and Moreover," Curr. Pharm. Des. (Id.) (2013).

Lieber et al., "Carbanoyl Azides,"Chem. Rev., 65(3):377-384 (1965).

Lion, CJ et al. Synthesis, Antitumor Evaluation, and Apoptosis-Inducing Activity of Hydroxylated €-Stillbenes. Journal of Medical Chemistry, vol. 48, 2005, pp. 1292-1295 [online], [retrieved on Apr. 13, 2015]. Retrieved from the Internet <URL: http:pubs.acs.org/doi/abs/10.1021/jm049238e>; p. 1293, scheme 1; p. S2, paragraph 3; p. S3, paragraph 1.

Matsunami et al., "A family of Candidate Taste Receptors in Human and Mouse," Nature 404(6778);601-4 (2000).

Reington, The Science and Practice of Pharmacy, 19th Ed. 1:176-177 (1995).

Shilin Xu, Xiaoxi Zhuang, Xiaofen Pan, Zhang Zhang, Lei Duan, Yingxue Liu, Lianwen Zhang, Xiaomei Ren, and Ke Ding, "1-Phenyl-4-benzoyl-1H-1,2,3-triazoles as Orally Bioavailable Transcriptional Function Suppressors of Estrogen-Related Receptoptor o" J. Med. Chem, 56(11):4631-4640 (2013).

Smith, et al. in an article entitled "GRAS Flavoring Substances 21," Food Technology, 57(5):46-59 (2003).

Wong et al., "Transduction of Bitter and Sweet Taste by Gustducin," Nature 361:796-800 (1996).

Kaldor et al. "Alkali Carbonate Effects on N-(-2-Hydroxyethyl)urea Cyclization: Application to a 2-Imidazolidinone Scale Up," Journal of Heterocyclic Chemistry, vol. 50, No. 4, Jul. 1, 2013, pp. 863-867.

* cited by examiner

PROCESS FOR THE SYNTHESIS OF SUBSTITUTED 1-BENZYL-3-(1-(ISOXAZOL-4-YLMETHYL)-1H-PYRAZOL-4-YL)IMIDAZOLIDINE-2,4-DIONES

This application is a divisional of U.S. Utility application Ser. No. 14/619,458 filed Feb. 11, 2015, which claims the priority benefit of U.S. Provisional Patent Application Ser. No. 61/938,861, filed Feb. 12, 2014, both of which are hereby incorporated by reference in their entireties.

FIELD OF THE INVENTION

The present invention relates to intermediates and processes for the preparation of compounds of formula (I) or their salts, as described infra. An exemplary use of these intermediate compounds is for the synthesis of taste (e.g., bitter blocking) modulatory compounds such as the exemplary compound shown below. However, it should be understood that these intermediate compounds may be used to produce other compounds which may be useful in other applications.

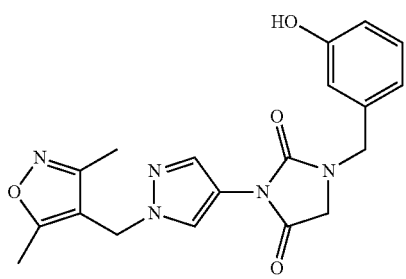 [SMILES: Cc1noc(C)c1Cn1cc(N2C(=O)CN(Cc3cccc(O)c3)C2=O)cn1]

BACKGROUND OF THE INVENTION

For centuries, various natural and unnatural compositions and/or compounds have been added to foods, beverages, and/or comestible (edible) compositions to improve their taste. It has long been known that there are only a few basic types of "tastes" (sweet, sour, bitter, salty, and "umami"/savory). Sour and salty tastes are mediated by channel-type receptors. Sweet, bitter and umami tastes are mediated by G-protein coupled receptors (GPCRs) and second-messenger signaling cascades (Iwata et al., "Taste Transductions in Taste Receptor Cells: Basic Tastes and Moreover," *Curr. Pharm. Des.* (Id.) (2013)).

One of the basic taste modalities that humans can recognize is bitter. The physiology of bitter and other taste modalities has become much better understood over the last decade, it is now known that bitter compounds elicit bitter taste by interacting with a family of cell surface receptors which belong to the superfamily of seven transmembrane domain receptors that interact with intracellular G proteins. Particularly, it is known that bitter ligands interact with one or more members of a family of GPCRs generally referred to in the art as T2Rs or TAS2R's.

The T2Rs are expressed in humans, rodents and other mammals (Adler et al., "A Novel Family of Mammalian Taste Receptors," *Cell* 100(6):693-702 (2000); Chandrashekar et al., "T2Rs Function as Bitter Taste Receptors," *Cell* 100(6):703-711 (2000); Matsunami et al., "A family of Candidate Taste Receptors in Human and Mouse," *Nature* 404(6778):601-4 (2000)).

Human and other mammalian T2R genes are specifically expressed in subset of taste receptor cells of the tongue and palate epithelia. T2Rs are activated by gustducin, a G protein specifically expressed in taste cells and linked to bitter stimuli transduction (Wong et al., "Transduction of Bitter and Sweet Taste by Gustducin," *Nature* 381:796-800 (1996)). Gustducin activation by mT2R5 occurs only in response to cycloheximide (Chandrashekar et al., "T2Rs Function as Bitter Taste Receptors," *Cell* 100(6): 703-711 (2000)). The amino acid and nucleic acid sequences of hT2Rs have been previously reported and are disclosed in published PCT applications by Zuker et al. (WO 01/18050 A2, (2001)), U.S. Pat. No. 7,105,650 by Adler et al. and (WO 01/77676 A1 (2001) by Adler et al.) as well as in Senomyx U.S. Pat. Nos. 8,524,464; 8,445,692; 8,338,115; 8,318,447; 8,273,542; 8,221,987; 8,153,386; 8,076,491; 8,071,320; 8,030,468; 8,030,451; 8,030,009; 8,030,008; 8,017,751; 7,968,693; 7,939,671; 7,939,276; 7,932,058; 7,927,823; 7,915,003; 7,883,856; 7,816,093; 7,811,788; 7,794,959; 7,785,802; 7,776,561; 7,736,862; 7,723,481; 7,723,051; 7,718,383; 7,704,698; 7,638,289; 7,517,972; 7,407,765; 7,399,601; 7,396,651; 7,393,654; and 7,022,488; all of which are incorporated by reference in their entirety herein.

To date, 23 human T2R genes are known to be functional and have been deorphaned by various groups including the present assignee Senomyx Inc. High throughput screening methods have been used to identify compounds that activate or modulate, preferably block, bitter taste elicited by the interaction of specific bitter ligands and hT2Rs. hT2R blockers are useful as potential additives for incorporation in various foods, beverages, nutraceuticals, medicaments and other comestibles.

For example, in U.S. application Ser. No. 10/191,058 incorporated by reference herein in its entirety, the present assignee used high throughput screening assays to discover bitter ligands that specifically activate different human T2Rs. Additionally, in U.S. application Ser. No. 11/455,693, incorporated by reference herein, the present assignee further identified bitter ligands that specifically activate other human T2Rs.

Also, in International Application Publication No. WO 2011/106114 to Karanewsky et al., assigned to Senomyx, Applicants described the identification and synthesis of many bitter antagonist compounds. Further this PCT application disclosed a means for synthesis of substituted 1-benzyl-3-(1-(isoxazol-4-ylmethyl)-1H-pyrazol-4-yl)imidazolidine-2,4-diones by the synthetic scheme depicted schematically in FIG. 1 (WO 2011/106114) ("'114 PCT Application"). The synthetic procedure disclosed in the '114 PCT Application differs from the synthetic process which is in part the focus of this application. This previous process included a number of steps and in particular included a step resulting in the formation of N-benzylglycine ester 4'a; N-alkylation of a 4-carboxypyrazole 5'a; in situ preparation of isocyanate 10'a via a Curtius rearrangement; quenching of the intermediate 10'a with ester 4'a and cyclization to form the hydantoin moiety (11'a), and finally deprotection of the phenolic silyl ether and recrystallization from ethanol resulting in the formation of the compound referred to in the FIG. 1 as 12'a.

While this synthetic procedure is useful, it has features which may be problematic, especially insofar as its usage for large scale synthesis. For example, this synthesis procedure involves the use of hazardous hydrazine. In addition, the process includes a Curtius rearrangement which potentially presents safety problems associated with the uncontrolled release of nitrogen (Lieber et al., "Carbamoyl Azides," *Chem. Rev.*, 65(3):377-384 (1965); Anon., Sichere Chemiarb., 1984, 36, 143-144). Therefore, in part based on these disadvantageous features, there is a need for improved methods for the synthesis of substituted 1-benzyl-3-(1-(isoxazol-4-ylmethyl)-1H-pyrazol-4-yl)imidazolidine-2,4-diones, especially methods that are suitable for large scale synthesis of these compounds. The present invention achieves these objectives.

SUMMARY OF THE INVENTION

Toward that end, the present invention generally relates to the development of improved methods for synthesizing substituted 1-benzyl-3-(1-(isoxazol-4-ylmethyl)-1H-pyrazol-4-yl)imidazolidine-2,4-diones, preferably substituted 1-benzyl-3-(1-(isoxazol-4-ylmethyl)-1H-pyrazol-4-yl)imidazolidine-2,4-diones compounds possessing bitter taste antagonistic properties.

A more specific aspect of the present invention relates to a process for the preparation of a compound of formula (I):

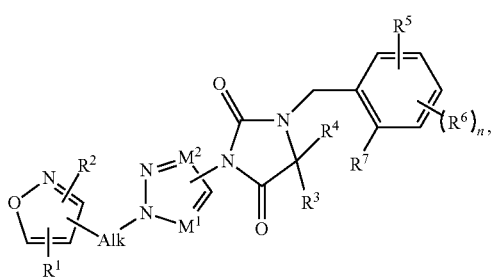

or a salt or oxide thereof.
wherein Alk is an alkyl group;
$M^1$ is N or $CR^8$, wherein $R^8$ is H or substituted or unsubstituted alkyl;
$M^2$ is N or $CR^9$, wherein $R^9$ is H or substituted or unsubstituted alkyl;
$R^1$ is selected from the group consisting of H, substituted or unsubstituted alkyl, substituted or unsubstituted heteroalkyl, substituted or unsubstituted alkoxy, and substituted or unsubstituted alkylaryl;
$R^2$ is selected from the group consisting of H, substituted or unsubstituted alkyl, substituted or unsubstituted heteroalkyl, substituted or unsubstituted alkoxy, and substituted or unsubstituted alkylaryl;
$R^3$ and $R^4$ are, the same or different from one another and are independently selected from the group consisting of H, substituted or unsubstituted alkyl, substituted or unsubstituted cycloalkyl, substituted or unsubstituted heterocycloalkylalkyl, substituted or unsubstituted aryl, and substituted or unsubstituted heteroalkyl, or $R^3$ and $R^4$, together with the carbon atom to which they are attached, form a substituted or unsubstituted cycloalkyl group;
$R^5$ is selected from the group consisting of H, substituted or unsubstituted alkyl, substituted or unsubstituted heteroalkyl, substituted or unsubstituted heteroalkylaryl, —OH, and —OPG;
$R^6$ is independently selected at each location from the group consisting of H, substituted or unsubstituted alkyl, substituted or unsubstituted heteroalkyl, substituted or unsubstituted heteroalkylaryl, —OH, and —OPG;

$R^7$ is selected from the group consisting of H, substituted or unsubstituted alkyl, substituted or unsubstituted heteroalkyl, substituted or unsubstituted heteroalkylaryl, —OH, and —OPG;
or $R^4$ and $R^7$ can combine to form —$(CH_2)_m$—;
PG is any protecting group;
n is 0, 1, 2, or 3; and
m is 0 or 1;
said process comprising:
treating a first intermediate compound of formula (II) wherein LG is a leaving group, and Alk, $M^1$, $M^2$, $R^1$, and $R^2$ are defined supra:

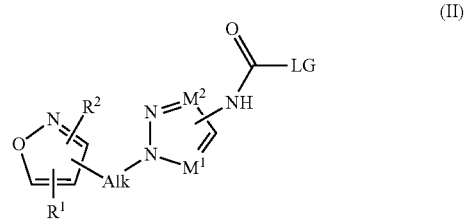

under conditions effective to form the compound of formula (I).

Another aspect of the present invention relates to compounds of formula (II):

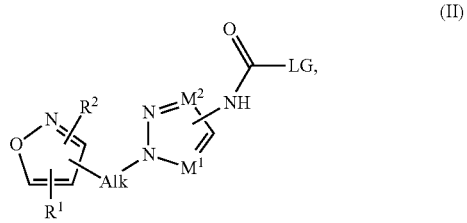

wherein Alk is an alkyl group;
$M^1$ is N or $CR^8$, wherein $R^8$ is H or substituted or unsubstituted alkyl;
$M^2$ is N or $CR^9$, wherein $R^9$ is H or substituted or unsubstituted alkyl;
$R^1$ is selected from the group consisting of H, substituted or unsubstituted alkyl, substituted or unsubstituted heteroalkyl, substituted or unsubstituted alkoxy, and substituted or unsubstituted alkylaryl;
$R^2$ is selected from the group consisting of H, substituted or unsubstituted alkyl, substituted or unsubstituted heteroalkyl, substituted or unsubstituted alkoxy, and substituted or unsubstituted alkylaryl; and
LG is selected from the group consisting of imidazolyl, O-alkyl, O-aryl, O-heteroaryl, O-alkyaryl, O-halogenated alkyl, and halo,
or an oxide thereof a salt thereof or a solvate thereof preferably an oxide, salt or solvate suitable for animal or human consumption.

Another exemplary aspect of the invention relates to the incorporation of compounds synthesized according to the invention, e.g., bitter antagonist compounds, into desired compositions, e.g., compositions for human or animal consumption, e.g., foods, beverages, nutraceuticals, medicaments and other comestibles. In addition, the invention relates to compositions containing compounds produced according to the invention, e.g., compositions suitable for human or animal consumption, e.g., foods, beverages, nutraceuticals, medicaments and other comestibles produced by such methods.

DETAILED DESCRIPTION OF THE INVENTION

Figure 1:
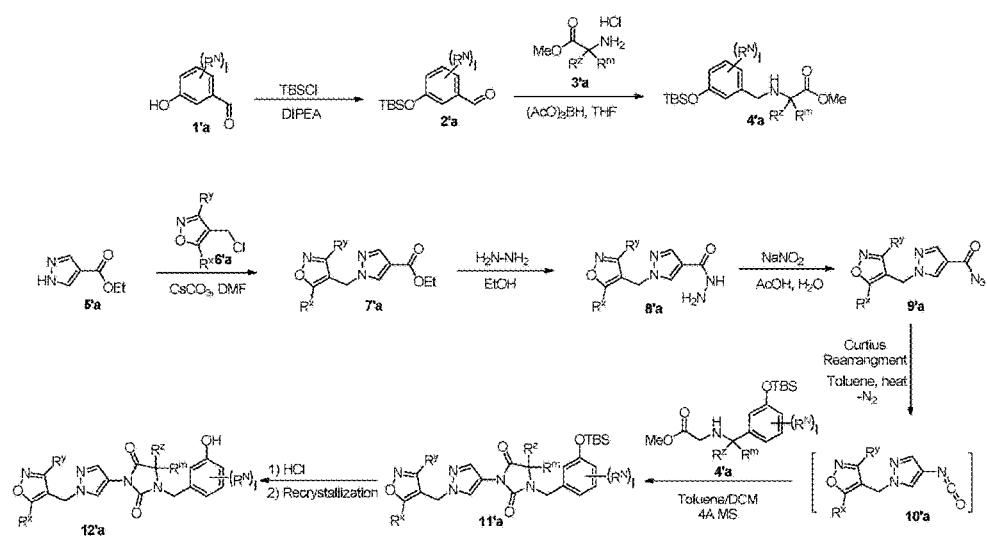
FIG. 1 depicts schematically the current method for synthesizing substituted 1-benzyl-3-(1-(isoxazol-4-ylmethyl)-1H-pyrazol-4-yl)imidazolidine-2,4-diones.
Figure 2:
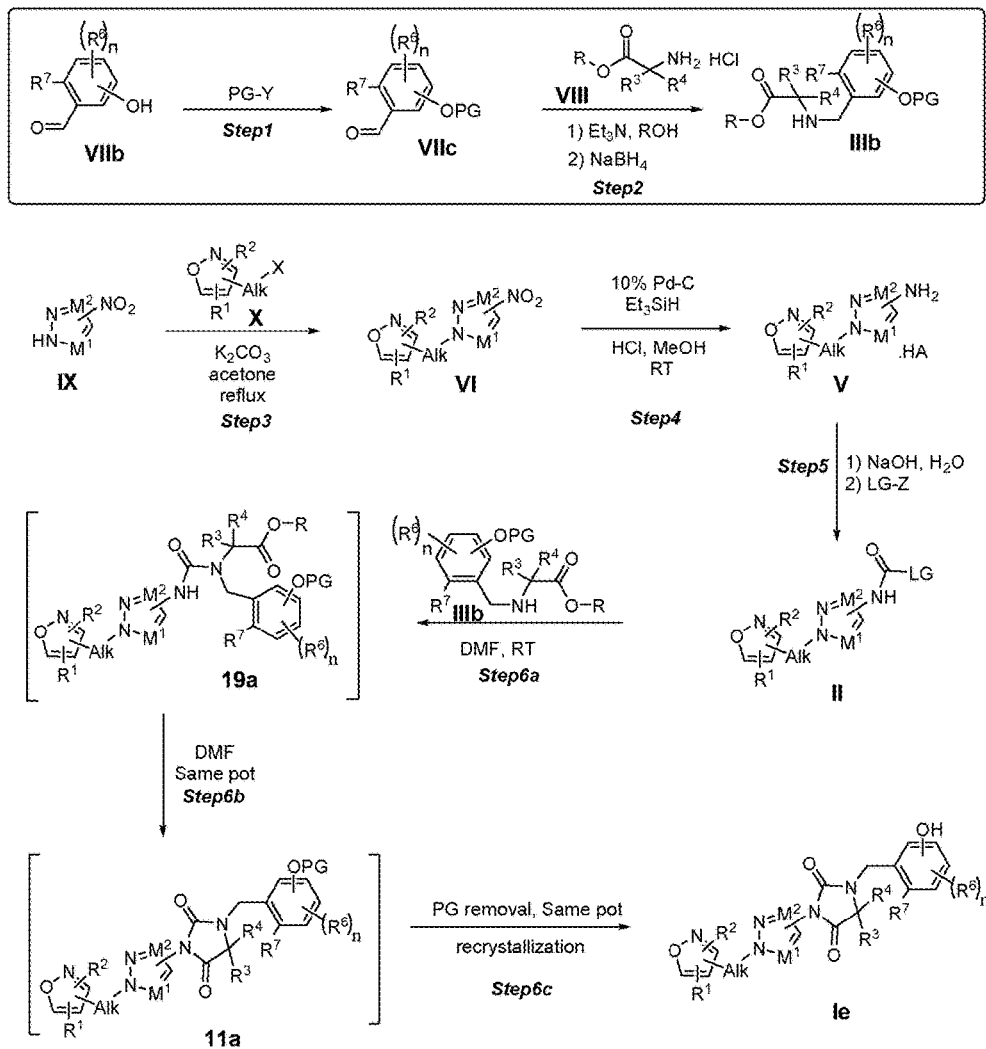
FIG. 2 shows the improved method for synthesizing substituted 1-benzyl-3-(1-(isoxazol-4-ylmethyl)-1H-pyrazol-4-yl)imidazolidine-2,4-diones according to the present invention.
Figure 3:
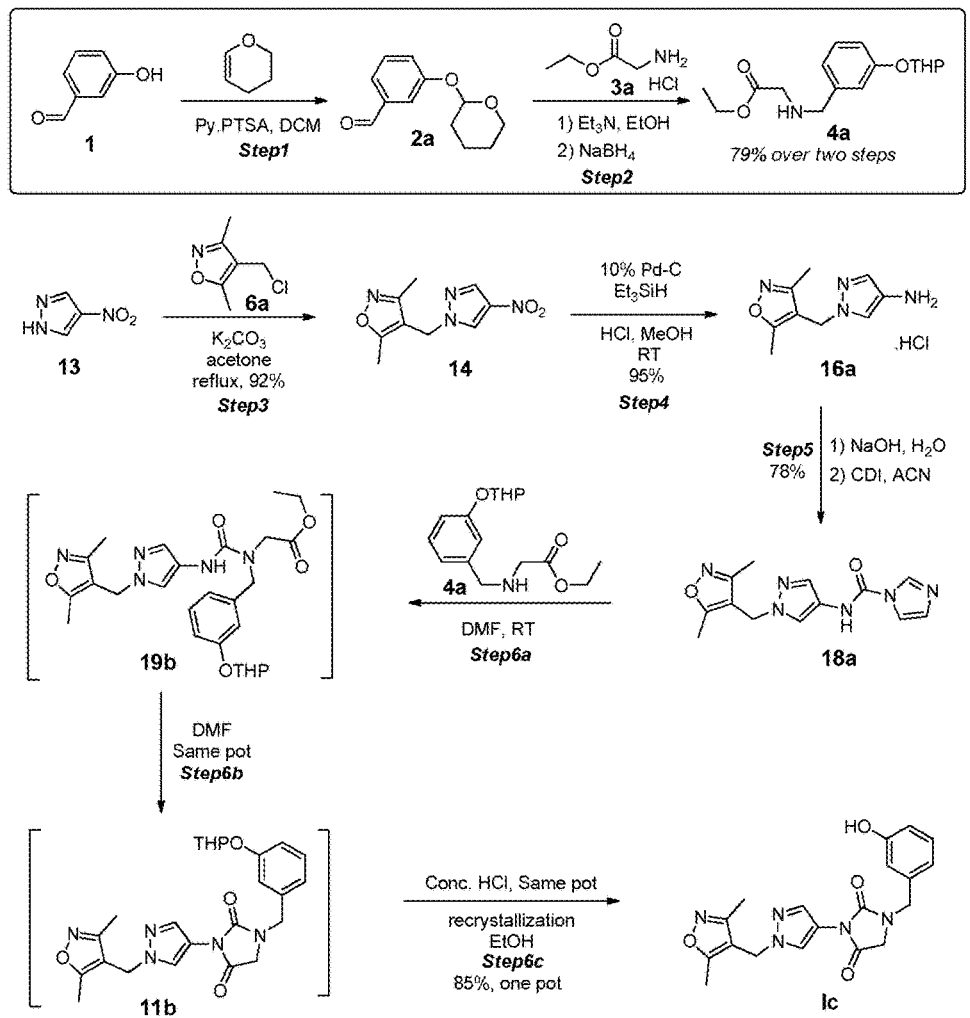
FIG. 3 depicts schematically the synthesis of a preferred 3-(1-((3,5-dimethylisoxazol-4-yl)methyl)-1H-pyrazol-4-yl)-1-(3-hydroxybenzyl)imidazolidine-2,4-dione compound according to the invention.
Figure 4:
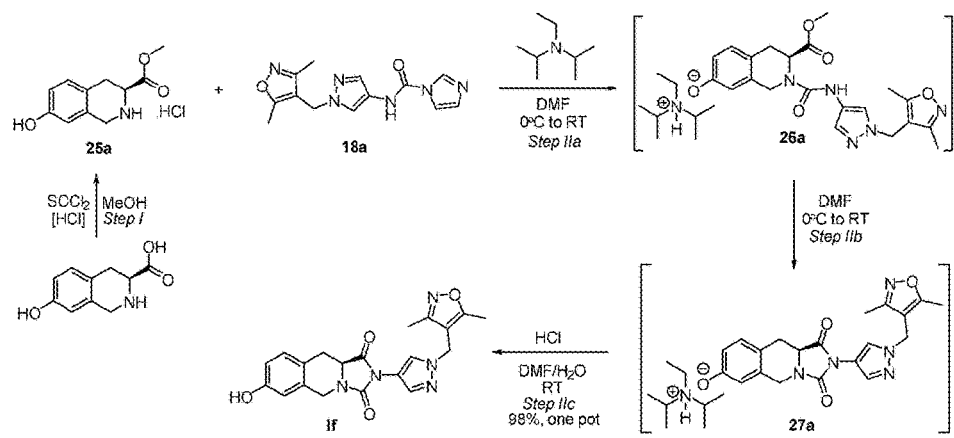
FIG. 4 depicts schematically the synthesis of (S)-2-(1-((3,5-dimethylisoxazol-4-yl)methyl)-1H-pyrazol-4-yl)-7-hydroxy-10,10a-dihydroimidazo[1,5-b]isoquinoline-1,3(2H,5H)-dione compound according to the invention.
Figure 5:
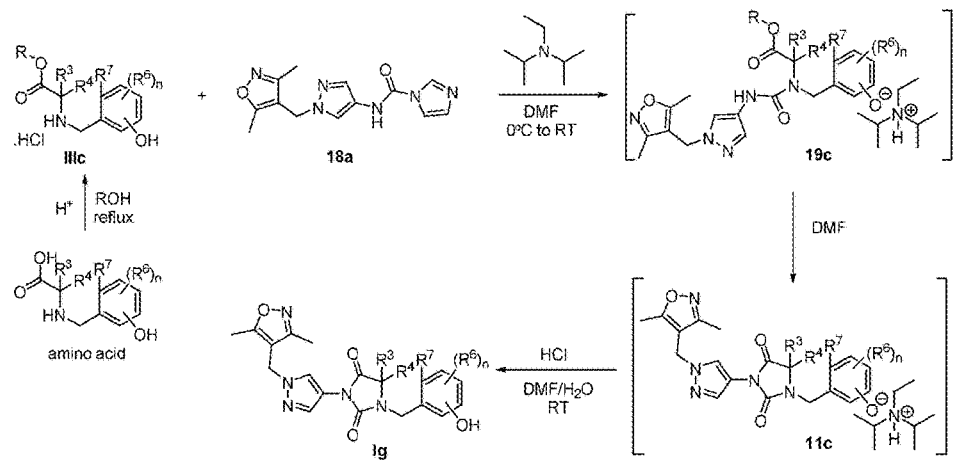
FIG. 5 shows schematically method for synthesizing substituted 1-benzyl-3-(1-(isoxazol-4-ylmethyl)-1H-pyrazol-4-yl)imidazolidine-2,4-diones according to the present invention.

One aspect of the present invention relates to a process for the preparation of a compound of formula (I):

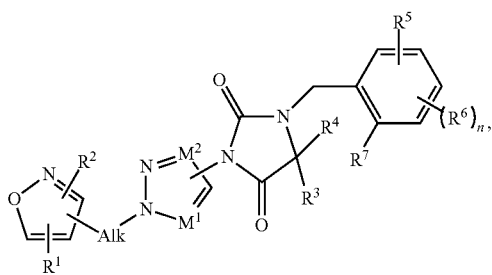

or a salt or oxide thereof,
wherein Alk is an alkyl group;
$M^1$ is N or $CR^8$, wherein R is H or substituted or unsubstituted alkyl;
$M^2$ is N or $CR^9$, wherein $R^9$ is H or substituted or unsubstituted alkyl;
$R^1$ is selected from the group consisting of H, substituted or unsubstituted alkyl substituted or unsubstituted heteroalkyl, substituted or unsubstituted alkoxy, and substituted or unsubstituted alkylaryl;
$R^2$ is selected from the group consisting of H, substituted or unsubstituted alkyl substituted or unsubstituted heteroalkyl, substituted or unsubstituted alkoxy, and substituted or unsubstituted alkylaryl;
$R^3$ and $R^4$ are, the same or different from one another and are independently selected from the group consisting of H, substituted or unsubstituted alkyl, substituted or unsubstituted cycloalkyl, substituted or unsubstituted heterocycloalkylalkyl, substituted or unsubstituted aryl and substituted or unsubstituted heteroalkyl, or $R^3$ and $R^4$, together with the carbon atom to which they are attached, form a substituted or unsubstituted cycloalkyl group;
$R^5$ is selected from the group consisting of H, substituted or unsubstituted alkyl, substituted or unsubstituted heteroalkyl, substituted or unsubstituted heteroalkylaryl, —OH, and —OPG;
$R^6$ is independently selected at each location from the group consisting of H, substituted or unsubstituted alkyl, substituted or unsubstituted heteroalkyl, substituted or unsubstituted heteroalkylaryl, —OH, and —OPG;
$R^7$ is selected from the group consisting of H, substituted or unsubstituted C alkyl, substituted or unsubstituted heteroalkyl, substituted or unsubstituted heteroalkylaryl, —OH, and —OPG;
or $R^4$ and $R^7$ can combine to form —$(CH_2)_m$—,
PG is any protecting group;
n is 0, 1, 2, or 3; and
m is 0 or 1;
said process comprising:
treating a first intermediate compound of formula (II) wherein LG is a leaving group, and Alk, $M^1$, $M^2$, $R^1$, and $R^2$ are defined supra:

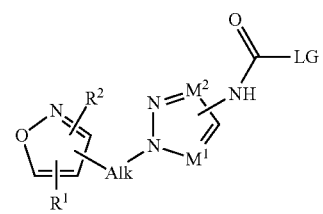

under conditions effective to form the compound of formula (I).

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, and the like.

The term "cycloalkyl" means a non-aromatic, saturated or unsaturated, mono- or multi-cyclic ring system of about 3 to about 7 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "alkenyl" means an aliphatic hydrocarbon group containing a carbon-carbon double bond and which may be straight or branched having about 2 to about 6 carbon atoms in the chain. Particular alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. The term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Particular alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "alkylaryl" means an alkyl residue attached to an aryl ring. Examples are benzyl, phenethyl, and the like.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

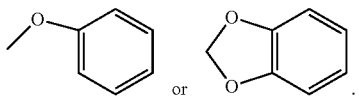

The term "cycloalkylalkyl" means a cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

The term "halogen" or "halo" refers to fluorine, chlorine, bromine, or iodine.

The term "haloalkyl" or "halogenated alkyl" means both branched and straight-chain alkyl substituted with one or more halogen, wherein the alkyl group is as herein described.

The term "arylalkoxy" means an aryl group bonded to an alkoxy group.

The term "heteroalkyl" or "heteroalkenyl" refers to alkyl or alkenyl, respectively, in which one or more of the carbon atoms (and optionally any associated hydrogen atoms), are each, independently of one another, replaced with the same or different heteroatoms or heteroatomic groups. Similarly, "heteroalkylene", or "heteroalkenylene" refers to alkylene or alkenylene, respectively, in which one or more carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms and heteroatomic groups may be placed at any interior position of the alkyl or alkenyl. Typical heteroatomic groups which can be included in these groups include, but are not limited to, —O—, —S—, —O—O—, —S—S—, —O—S—, —N(R$^a$)$_2$—, =N—N=, —N=N—, —N=N—N(R$^a$)$_2$—, —P(O)$_2$—, —POR$^a$—, —O—P(O)$_2$—, —SO—, —SO$_2$—, —Sn(R$^a$)$_2$— and the like, where each R$^a$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, or a protecting group.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "heteroarylalkyl" means a heteroaryl group to which an alkyl group is attached.

The term "heteroalkylaryl" means a heteroalkyl group to which an aryl group is attached.

The term "heterocycloalkyl" refers to a cycloalkyl group in which at least one of the carbon atoms in the ring is replaced by a heteroatom (e.g., O, S or N).

The term "heterocycloalkylalkyl" means a heterocycloalkyl group to which an alkyl group is attached.

The term "leaving group" herein means a chemical group readily displaceable with appropriate reactants under compound conventional reaction conditions well known to those skilled in the art of organic synthesis. Typical suitable leaving groups include but are not limited to imidazolyl, O-alkyl, O-aryl, O-heteroalkyl, O-heteroaryl, —O—CH$_2$CF$_2$H, —O—CH$_2$CCl$_2$H, —O—CH$_2$CF$_3$, and —O—CH$_2$CCl$_3$, benzotriazolyl, oxide, halide, trifluoromethylsulfonyloxy, methylsulfonyloxy and 4-methyl-phenylsulfonyloxy.

The term "monocyclic" used herein indicates a molecular structure having one ring.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, alkylaryl or alkylheteroaryl groups, aralkoxy or heteroaralkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted alkylaryl," either the aryl or the alkyl group may be substituted, or both the aryl and the alkyl groups may be substituted with one or more substituents. Additionally, in some cases, suitable substituents may combine to form one or more rings as known to those of skill in the art.

The term "compound," "product compound," and equivalent expressions, is meant to embrace compounds of general formula I as hereinbefore described. Also contemplated are salts, oxides, and solvates thereof, preferably those suitable for mammalian or human consumption, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy,* 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. In some preferred embodiments the compounds are provided as the salt form. Similarly, with respect to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutical composition" means a composition comprising a compound of formula I (added as a flavor additive or modulator) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compounds described herein, and includes, for example, tablets, dragées, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "salt" or "salt suitable for animal or human consumption" means derivatives of the disclosed compounds wherein the parent compound is modified by making acid or base salts thereof. In most instances, the term refers to salts prepared from non-toxic acids or bases including inorganic acids and bases and organic acids and bases. Suitable acid addition salts for the compounds described herein include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds described herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Salts and salts suitable for animal or human ingestion include, but are not limited to, amine salts, such as but not limited to N, N'dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula $C=C(OR)$ where R is hydrogen, alkyl, alkenyl, alkynyl, aryl, heteroaryl, cycloalkyl, or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

Compounds described herein contain one or more double bonds and may thus give rise to cis/trans isomers as well as other conformational isomers. The present invention includes all such possible isomers as well as mixtures of such isomers.

Compounds described herein, and particularly the substituents described above, may contain one or more asymmetric centers and may thus give rise to diastereomers and optical isomers. The present invention includes all such possible diastereomers as well as their racemic mixtures, their substantially pure resolved enantiomers, all possible geometric isomers, and acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "solvate" means a compound, or a salt thereof, that further includes a stoichiometric or non-stoichiometric amount of solvent bound by non-covalent intermolecular forces. Where the solvent is water, the solvate is a hydrate.

The term "solvate" refers to a compound of formula I in the solid state, wherein molecules of a suitable solvent are incorporated in the crystal lattice. Suitable solvents include ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

As used herein, the term "analog thereof" in the context of the compounds disclosed herein includes diastereomers, hydrates, solvates, salts, and oxides of the compounds.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

In one embodiment of the present invention alkyl is $C_{1-6}$ alkyl.

In another embodiment of the present invention the leaving group is independently selected from the group consisting of imidazolyl, O-alkyl, O-aryl, O-heteroalkyl, and O-heteroaryl.

In another embodiment of the present invention $R^1$ and $R^2$ in formula I are independently selected from the group consisting of H, substituted or unsubstituted alkyl, substituted or unsubstituted heteroalkyl, substituted or unsubstituted alkoxy, and substituted or unsubstituted alkylaryl.

In yet another embodiment of the present invention $R^1$ and $R^2$ in formula I are methyl.

In a further embodiment of the present invention the protecting group is independently selected from the group consisting of tetrahydropyranyl (THP), methoxymethyl (MOM), silyl, and benzyl.

In yet another embodiment of the present invention treating includes reacting the first intermediate with a second intermediate of formula (III):

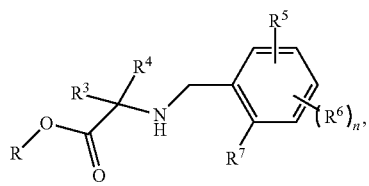

(III)

wherein R is selected from the group consisting of H, alkyl, ethyl, heteroalkyl, aryl, and heteroaryl, and $R^3$, $R^4$, $R^5$, $R^6$, $R^7$, and n are the same as defined in Claim 1.

In a further embodiment of the present invention the second intermediate has a formula (IIIa):

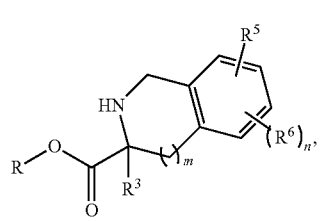

(IIIa)

wherein R is selected from the group consisting of H, alkyl, ethyl, heteroalkyl, aryl, and heteroaryl, and $R^3$, $R^5$, $R^6$, m, and n are the same as defined in Claim 1.

In another embodiment of the present invention the process further includes treating a third intermediate of formula (IV) or a salt thereof of formula (V):

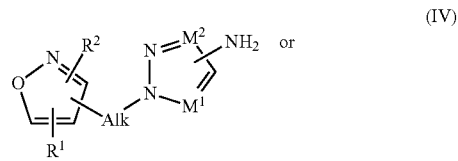

(IV)

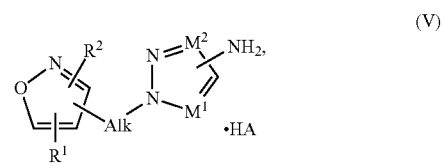

(V)

wherein Alk, $M^1$, $M^2$, $R^1$, and $R^2$ are the same as defined in Claim 1, under conditions effective to form the first intermediate compound.

In another embodiment of the present invention the third intermediate compound is of formula (IV):

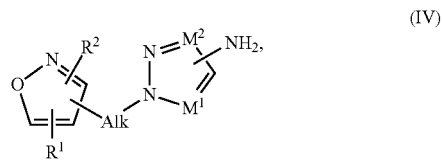

(IV)

wherein Alk, $M^1$, $M^2$, $R^1$, and $R^2$ are the same as defined in Claim 1, is treated with an acid to form a compound of formula (V):

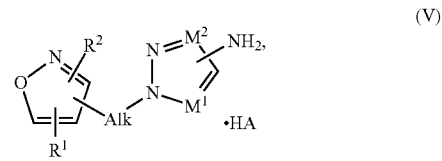

(V)

wherein Alk, $M^1$, $M^2$, $R^1$, and $R^2$ are the same as defined in Claim 1. Suitable acids according to this embodiment include, e.g., hydrochloric acid (HCl), hydrobromic acid (HBr), sulfuric acid ($H_2SO_4$), and trifluoroacetic acid (TFA).

In a further embodiment of the present invention the process further includes reacting

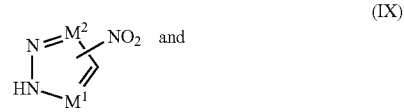

(IX)

-continued

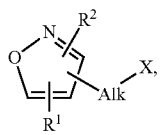

wherein X is selected from the group consisting of halogen and —OH and Alk, M¹, M², R¹, and R² are the same as defined in Claim 1, under conditions effective to form a fourth intermediate of formula (VI):

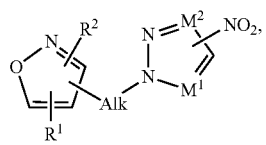

wherein Alk, M¹, M², R¹, and R² are the same as defined in Claim 1, and treating the fourth intermediate compound with a reducing agent under conditions effective to form the third intermediate compound. Suitable reducing agent according to this embodiment include, e.g., hydrogen in the presence of Pd/C, Pd/C-Et$_3$SiH, SnCl$_2$, and Fe.

In yet another embodiment of the present invention the compound of formula (I) is represented by formula (Ia):

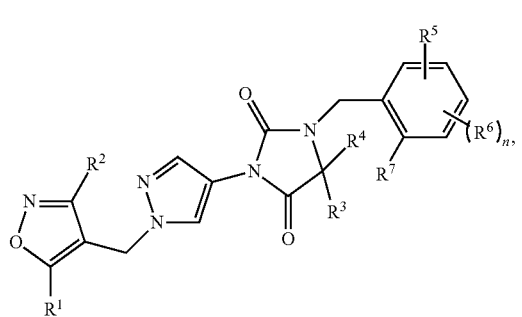

wherein R¹, R², R³, R⁴, R⁵, R⁶, R⁷ and n are the same as defined in Claim 1.

In another embodiment of the present invention the compound of formula (I) is represented by formula (Ib):

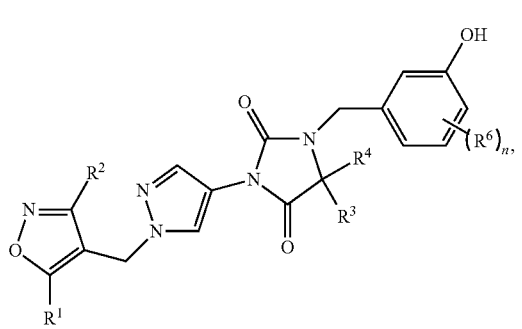

wherein R¹, R², R³, R⁴, R⁶, and n are the same as defined in Claim 1.

In another embodiment of the present invention the compound of formula (I) is represented by formula (Ic):

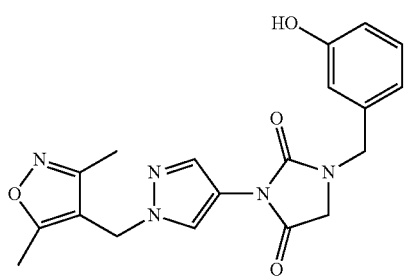

In yet another embodiment of the present invention the compound of formula (I) is represented by formula (Id):

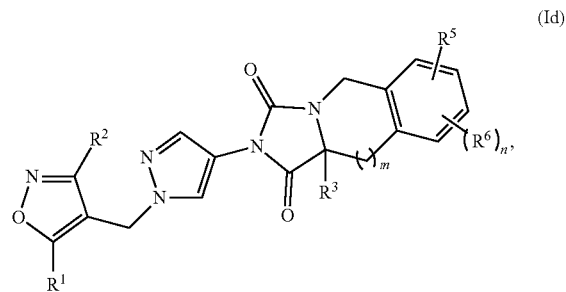

wherein R¹, R², R³, R⁵, R⁶, m, and n are the same as defined in Claim 1.

In a further embodiment of the present invention the process further includes providing a compound of formula (VII):

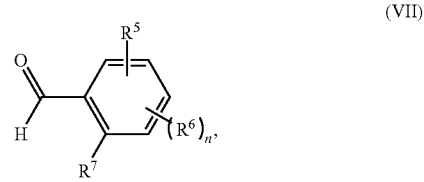

wherein R⁵, R⁶, R⁷, and n are the same as defined in Claim 1;

providing a compound of formula (VIII):

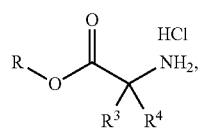

wherein R³ and R⁴ are the same as defined in Claim 1; and R is selected from the group consisting of H, alkyl, heteroalkyl, aryl, and heteroaryl; and reacting the compound of formula (VII) with the compound of formula (VIII) under conditions effective to form a 15 second intermediate of said formula (III).

In yet another embodiment of the present invention, the process further includes reacting the compound of formula (VIIa):

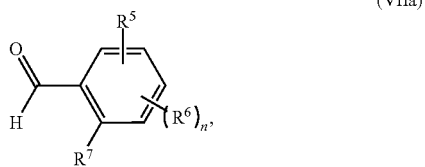

wherein R⁵, R⁶, R⁷, and n are the same as defined in Claim 1, with the proviso that one or more of the R⁵, R⁶, or R⁷ is OH; with a protecting group introducing agent (PG-Y) under conditions effective to form a compound of formula (VII). Suitable protecting group introducing agent (PG-Y) according to this embodiment include, e.g., methoxymethyl chloride (MOMCl), methoxymethyl bromide (MOMBr), dihydropyran (DHP), and tetrahydro-2H-pyran-2-ol.

In another embodiment of the present invention, the process further includes reacting the compound of formula (VII) with the compound of formula (VIII):

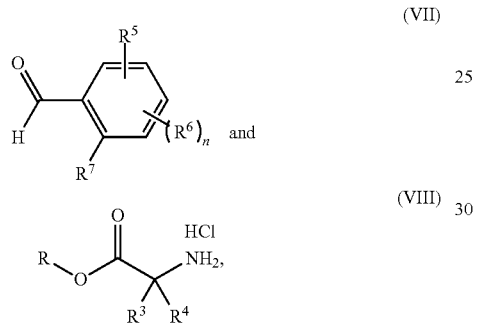

wherein R, R³, R⁴, R⁵, R⁶, R⁷, and n are as previously defined, under conditions effective to form a second intermediate represented by Formula (IIIa):

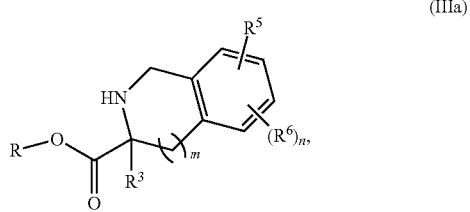

wherein R, R³, R⁵, R⁶, m, and n are the same as previously defined.

Another aspect of the present invention relates to a compound of formula (II):

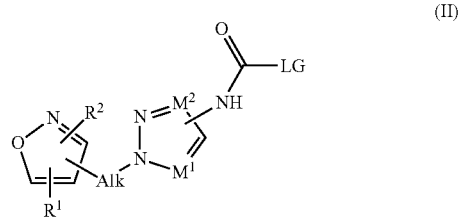

wherein Alk is an alkyl group;

M¹ is N or CR⁸, wherein R⁸ is H or substituted or unsubstituted alkyl;
M² is N or CR⁹, wherein R⁹ is H or substituted or unsubstituted alkyl;
R¹ is selected from the group consisting of H, substituted or unsubstituted alkyl, substituted or unsubstituted heteroalkyl, substituted or unsubstituted alkoxy, and substituted or unsubstituted alkylaryl;
R² is selected from the group consisting of H, substituted or unsubstituted alkyl, substituted or unsubstituted heteroalkyl, substituted or unsubstituted alkoxy, and substituted or unsubstituted alkylaryl; and
LG is selected from the group consisting of imidazolyl, O-alkyl, O-aryl, O-heteroaryl, O-alkyaryl, O-halogenated alkyl, and halo,
or an oxide thereof; a salt thereof; or a solvate thereof; thereof; preferably an oxide, salt or solvate suitable for animal or human consumption.

In one embodiment of the present invention, the compound of formula (II) is represented by formula (IIa):

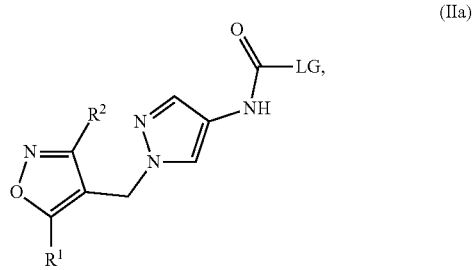

wherein LG, R¹, and R² are the same as defined in Claim 1.

In another embodiment of the present invention, the compound is selected from the group consisting of

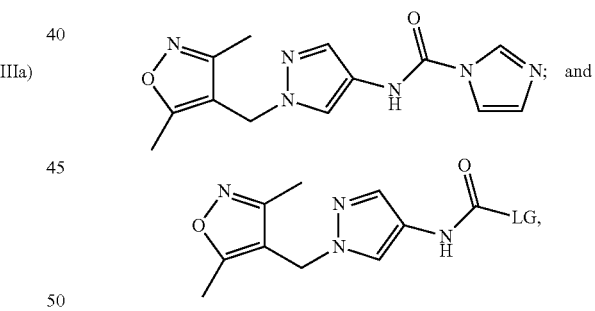

wherein
LG is selected from the group consisting of imidazolyl, O-alkyl, O-aryl, O-heteroaryl, O-alkyaryl, O-halogenated alkyl, and halo; or an oxide, salt, or solvate thereof.

Another embodiment of the present invention relates to a compound of formula (I) or a salt thereof, preferably one suitable for animal or human consumption, whenever it is prepared or produced by the above mentioned process or by an obvious chemical equivalent thereof.

Yet another embodiment of the present invention relates to a composition that includes a compound synthesized according to the above mentioned process or by an obvious chemical equivalent thereof.

Another embodiment of the present invention relates to the composition, wherein the compound is (Ia), or a salt, solvate, or an obvious chemical equivalent thereof, preferably a salt, solvate or chemical equivalent suitable for animal or human consumption.

Another embodiment of the present invention relates to the composition, wherein the compound is (Ib), or a salt, solvate, or an obvious chemical equivalent thereof; preferably a salt, solvate or chemical equivalent suitable for animal or human consumption.

Yet another embodiment of the present invention relates to the composition, wherein the compound is (Ic), or a salt, solvate, or an obvious chemical equivalent thereof; preferably a salt, solvate or chemical equivalent suitable for animal or human consumption.

Another embodiment of the present invention relates to the composition, wherein the compound is (Id), or a salt, solvate, or an obvious chemical equivalent thereof; preferably a salt, solvate or chemical equivalent suitable for animal or human consumption In a further embodiment of the present invention the composition further includes a carrier.

In yet another embodiment of the present invention the composition includes the compound is in an amount effective to reduce or alleviate a bitter taste.

In another embodiment of the present invention the concentration of the compound in the composition is from about 0.1 ppm to about 100 ppm.

In yet another embodiment of the present invention the concentration of the compound in the composition is from about 1 ppm to about 25 ppm.

In another embodiment of the present invention the composition is a food or beverage product, a pharmaceutical composition, a nutritional product, a dietary supplement, over-the-counter medication, or oral care product.

In a further embodiment of the present invention the composition has a reduced or alleviated bitter taste as compared to a composition not containing the compound, as judged by a majority of a panel of at least eight human taste testers.

In yet another embodiment of the present invention the composition is for human or animal consumption.

In a further embodiment of the present invention a method of altering or improving the taste of a composition includes adding to the composition at least one compound prepared by the method according to the above mentioned process or by an obvious chemical equivalent thereof, in an amount effective to obtain a modified composition having altered or improved taste relative to an otherwise identical composition lacking the compound.

Yet another embodiment of the present invention relates to the method of reducing or alleviating the bitter taste of the composition.

Another embodiment of the present invention relates to the method, wherein the compound is (Ia), or a salt, solvate, or an obvious chemical equivalent thereof, preferably a salt, solvate or chemical equivalent suitable for animal or human consumption.

Yet another embodiment of the present invention relates to the method, wherein the compound is (Ib), or a salt, solvate, or an obvious chemical equivalent thereof, preferably a salt, solvate or chemical equivalent suitable for animal or human consumption.

Another embodiment of the present invention relates to the method, wherein the compound is (Ic), or a salt, solvate, or an obvious chemical equivalent thereof, preferably a salt, solvate or chemical equivalent suitable for animal or human consumption.

Yet another embodiment of the present invention relates to the method, wherein the compound is (Id), or a salt, solvate, or an obvious chemical equivalent thereof, preferably a salt, solvate or chemical equivalent suitable for animal or human consumption.

In another embodiment of the present invention the compound is in an amount effective to reduce or alleviate a bitter taste.

In yet another embodiment of the present invention the modified composition has a reduced or alleviated bitter taste as compared to the composition not containing the compound prepared by the method according to the above mentioned process or by an obvious chemical equivalent thereof, as judged by a majority of a panel of at least eight human taste testers.

To generate the intermediate, N-benzylglycine ester (4) (Scheme 1, below), the hydroxyl group of 3-hydroxybenzaldehyde (1) is first protected with commercially available protecting agents following conventional protocols to form intermediate 2 (Shilin Xu, Xiaoxi Zhuang, Xiaofen Pan, Zhang Zhang, Lei Duan, Yingxue Liu, Lianwen Zhang, Xiaomei Ren, and Ke Ding, "1-Phenyl-4-benzoyl-1H-1,2, 3-triazoles as Orally Bioavailable Transcriptional Function Suppressors of Estrogen-Related Receptor a" *J. Med. Chem.* 56(11):4631-4640 (2013), which is hereby incorporated by reference in its entirety). The latter intermediate 2 is further reacted with compound 3 under reductive amination conditions to form the corresponding intermediate 4. Alternatively, compound 1 is reacted with 3 without the need of protecting groups to yield the corresponding unprotected phenol derivative 4 (U.S. Patent Application Publication No. 2010/254916 to Karanewsky et al., which is hereby incorporated by reference in its entirety).

Scheme 1

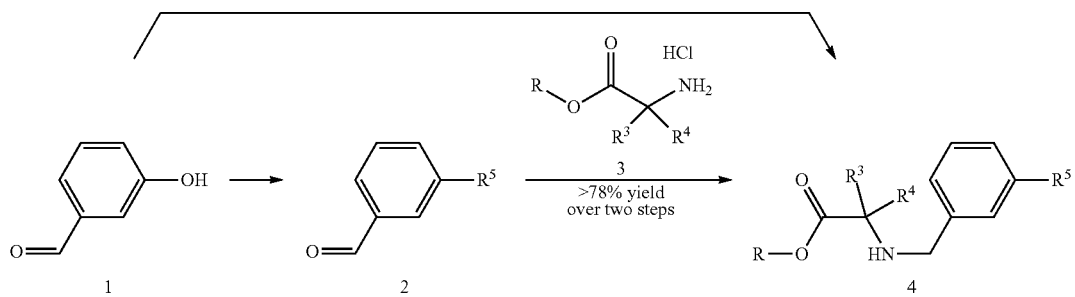

For the synthesis of compound 18 (Scheme 2, below), compound 13 is first reacted with compound 6 either under Mitsunobu conditions or using potassium carbonate, cesium carbonate or any suitable bases in acetone, DMF or other appropriate solvents to form the nitro derivative 14. The subsequent reduction of 14 is performed by hydrogenation in the presence of Pd/C or other reducing agents including but not limited to $SnCl_2$ or Fe to provide compound 1-((3,5-dimethylisoxazol-4-yl)methyl)-1H-pyrazol-4-amine (15) that is acidified in situ with any appropriate acid such as HCl, HBr, or $H_2SO_4$ to form the corresponding 1-((3,5-dimethylisoxazol-4-yl)methyl)-1H-pyrazol-4-amine salt (16). The use of some combinations of reagents such as Pd/C and triethylsilane significantly reduces the time necessary to complete the reduction of 14. Using these combinations of reagent also minimizes the formation of side product and, therefore, improves the reaction work up and the overall yield of 15 and its salt 16. Compound 16 can be treated with various bases to generate the free base 15 followed by addition of either commercially available CDI (compound which is hereby incorporated by reference in its entirety). In some cases compound 18 can precipitate directly out of the reaction mixture and be simply isolated by filtration (Scheme 2). The generation of compound 18 from compound 14 presents significant safety advantages over previously reported alternatives such as the synthesis of 18 from 9 (Scheme 2) (International Application Publication No. WO 2011/106114 to Karanewsky et al., which is hereby incorporated by reference in its entirety). In fact, the Curtius rearrangement necessary to convert the acyl azide 9 to 18 presents potential safety problems associated with the uncontrolled release of nitrogen (Lieber et al., "Carbamoyl Azides," Chem. Rev., 65(3):377-384 (1965); Anon., Sichere Chemiarb., 1984, 36, 143-144, which are hereby incorporated by reference in their entirety). Unfortunately, the reported representative large scale synthesis of (12'a) involves not only the used of hazardous hydrazine but also a Curtius rearrangement step (FIG. 1, International Application Publication No. WO 2011/106114 to Karanewsky et al., which is hereby incorporated by reference in its entirety).

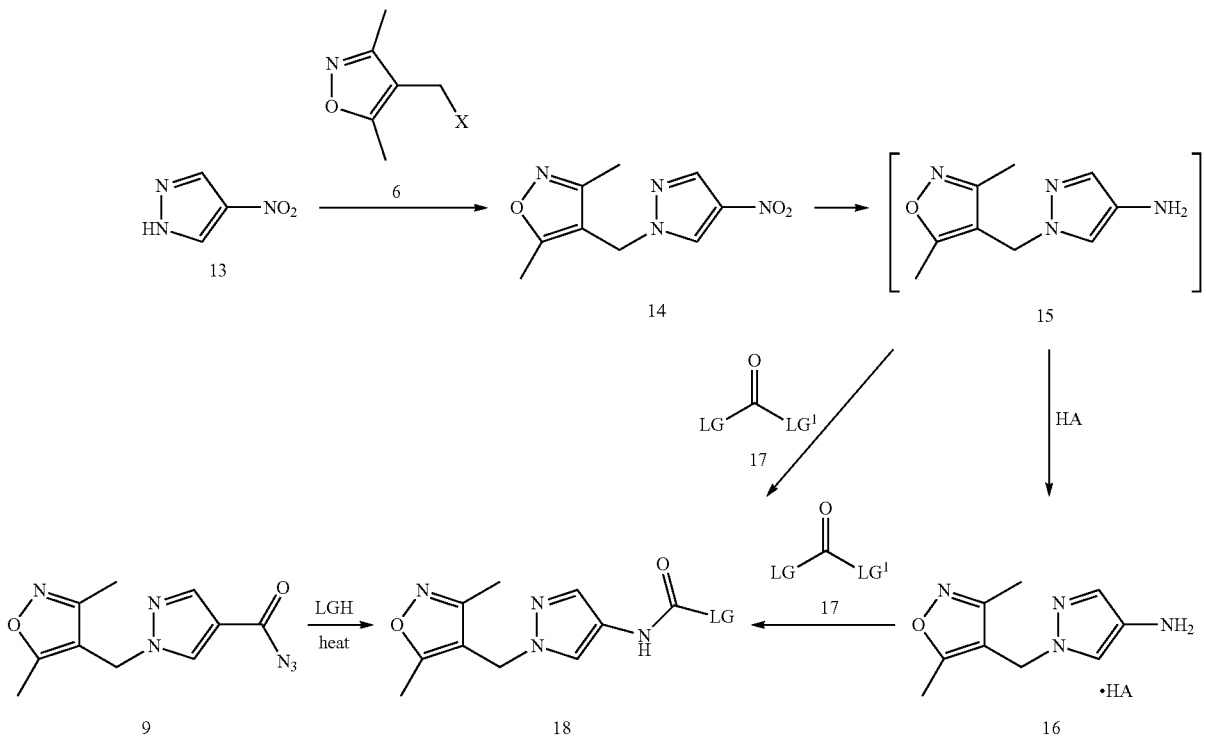

Scheme 2

X = Cl, Br, I, $OSO_2R^8$, OH
$R^8$ = Me, p-tolyl or any other appropriate substituent
LG = imidazolyl, O-alkyl, O-aryl, O-heteroalkyl or O-heteroaryl
LG1 = Cl, Br, imidazolyl
HA = any appropriate acid 17a, LG=LG¹=imidazolyl) to form the corresponding imidazolyl carboxamide 18a (LG=imidazolyl) or chloroformates and N-oxo-carbonate to form the corresponding carbamates 18 (LG=O-alkyl, O-aryl, O-heteroalkyl, O-heteroaryl, or oxide). Intermediates 18 can also be obtained directly from 1-((3,5-dimethylisoxazol-4-yl)methyl)-1H-pyrazol-4-amine (15) without need to generate the hydrochloride intermediate 16 (International Application Publication No. WO 2011/106114 to Karanewsky et al., As shown in Scheme 3, compound 18 and 4 may be permitted to react together in appropriate solvents such as DMF, DCM, and toluene with or without use of base to form intermediate 19. In exemplary embodiments this reaction is effected with heating, i.e., at elevated temperature (room temperature up to 110° C.). However, it is expected that the formation of 19 and its subsequent cyclization to the protected hydantoin 11 alternatively may be effected at lower temperature, e.g., room or ambient temperature, or lower (room temperature down to 0° C.). Although heating might be necessary, in some cases, the formation of 19 and its subsequent cyclization to the protected hydantoin 11 perform smoothly even at room temperature and below. The protected hydantoin 11 can be either isolated or deprotected in situ to yield the desired compound 12. Following the latter in situ strategy, the synthesis of intermediate 19 and its sequential conversion to 12 via the protected hydantoin 11 is performed very efficiently in one pot. A simple extraction or precipitation of 12 from the reaction mixture followed by recrystallization either from ethanol or other appropriate solvents furnish compound 12 in high yield and purity without any preliminary chromatographic cleaning.

Scheme 3

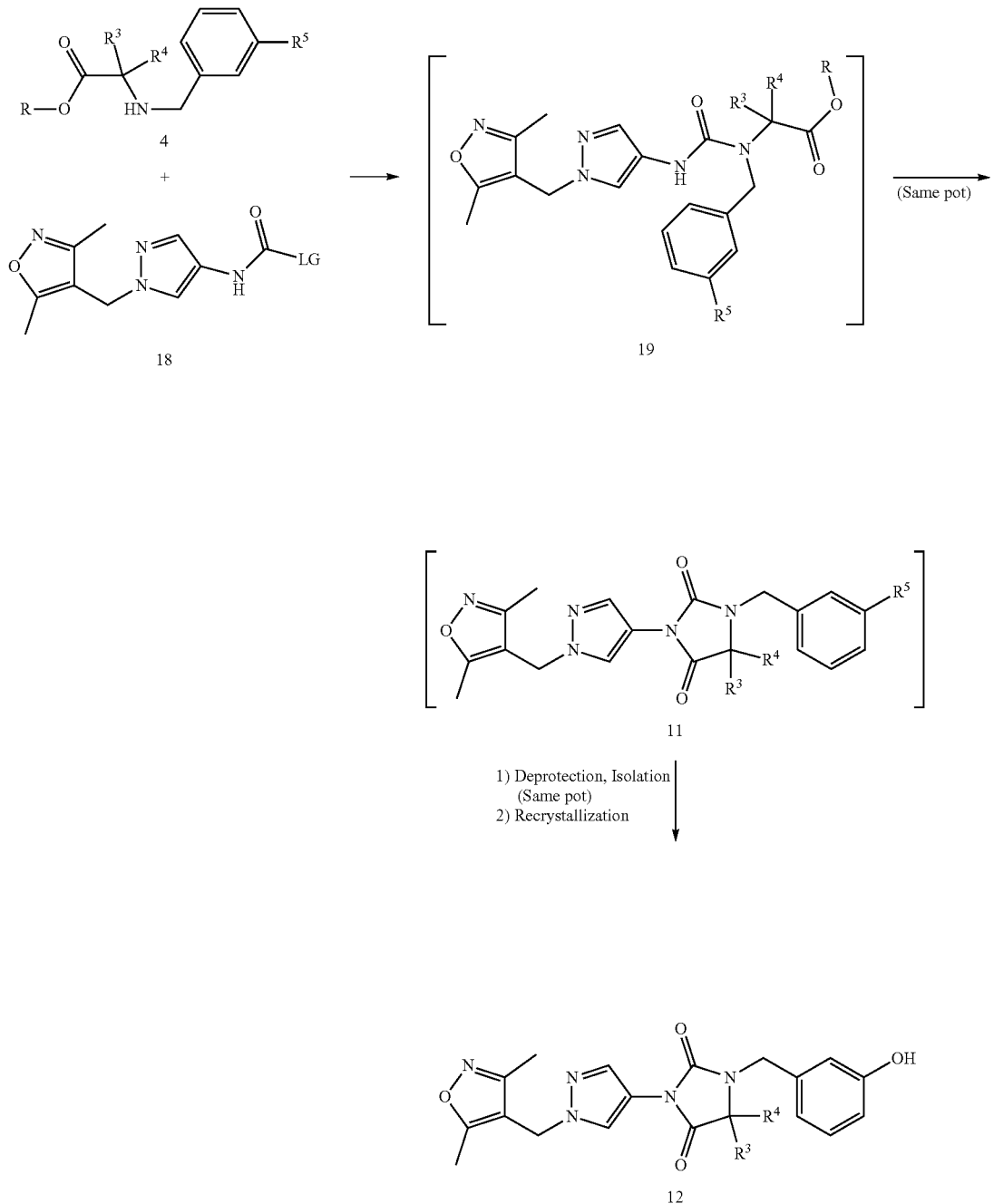

R = H, Alkyl, Heteroalkyl, Aryl, or Heteroaryl
$R^3$ = H, Alkyl, Heteroalkyl
$R^4$ = H, Alkyl, Heteroalkyl
$R^5$ = OH, OTHP, OMOM, O-silyl, OBz, or any OPG
LG = imidazolyl, O-alkyl, O-aryl, O-heteroalkyl or O-heteroaryl Compound 12 reacts with NaOH, NaHCO₃, Na₂CO₃, tert-BuONa, and other appropriate sodium complexes to for the corresponding sodium salts 20. Other suitable salt forms of compound 12 such as ammonium, potassium, calcium and magnesium can be obtained using appropriate procedures (Scheme 4).

Scheme 4

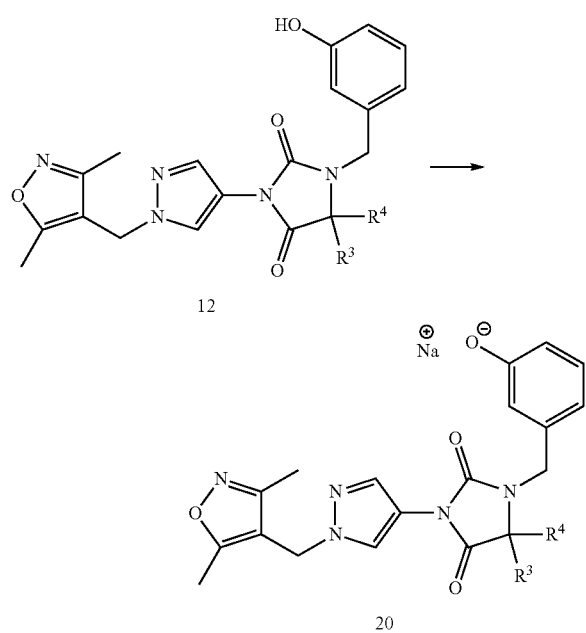

Preparation of other mono- and poly-substituted 1-benzyl-3-(1-((3,5-dimethylisoxazol-4-yl)methyl)-1H-pyrazol-4-yl)imidazolidine-2,4-dione is depicted in Scheme 5. Compound 21 reacts with compound 18 in appropriate solvents such as DMF, DCM, and toluene with or without use of base to form intermediate 22. Again while in exemplary embodiments this synthesis step is effected while heating (room temperature up to 110° C.), in some embodiments, the formation of 22 and its subsequent cyclization to the hydantoin 23 may be effected at room temperature or lower temperatures (room temperature down to 0° C.). In case $R^5$ and/or $R^6$ is a protected phenol, the protected hydantoin 23 can be either isolated or deprotected in situ to yield the desired compound 24. Following the latter in situ strategy, the synthesis of intermediate 22 and its conversion to the hydantoin 23 (or to the free phenol analog 24 via the protected hydantoin 23) is performed very efficiently in one pot. A simple extraction or precipitation of 24 from the reaction mixture followed by recrystallization either from ethanol or other appropriate solvents can furnish compound 24 in high yield and purity without any preliminary chromatographic cleaning.

Scheme 5

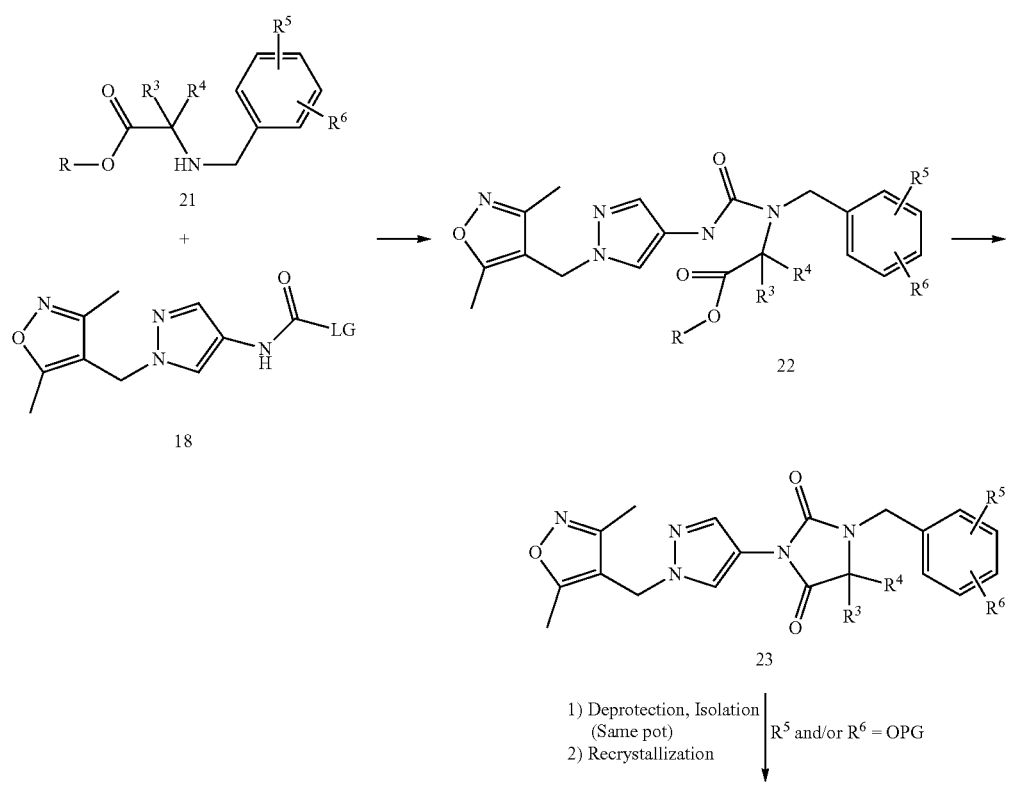

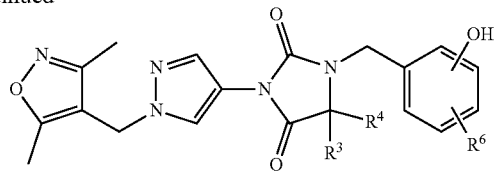

24

R = H, Alkyl, Heteroalkyl, Aryl, or Heteroaryl
R$^3$ = H, Alkyl, Heteroalkyl, Aryl, or Heteroaryl
R$^5$ = H, Alkyl, Heteroalkyl, OH, OPG
R$^6$ = H, Alkyl, Heteroalkyl, OH, OPG
LG = imidazolyl, O-alkyl, O-aryl, O-heteroalkyl or O-heteroaryl
PG = any protecting group Preparation of polycyclic 1-benzyl-3-(1-((3,5-dimethyl-isoxazol-4-yl)methyl)-1H-pyrazol-4-yl)imidazolidine-2,4-dione is shown in Scheme 6. Bicyclic building blocks 25 reacts with compound 18 in appropriate solvents such as DMF, DCM, and toluene with or without use of base to form intermediate 26. Again while in exemplary embodiments this synthesis step may be effected while heating (room temperature up to 110° C.), in some embodiments the formation of 26 and its subsequent cyclization to the tricyclic hydantoin 27 may be effected at room temperature or lower temperatures (room temperature down to 0° C.). In case R$^4$ and/or R$^5$ is a protected phenol, the protected hydantoin 27 can be either isolated or deprotected in situ to yield the corresponding polycyclic hydantoin 28. Following the latter in situ strategy, the synthesis of intermediate 26 and its conversion to the polycyclic hydantoin 27 (or to the free phenol analog 28 via the protected hydantoin 27) is performed very efficiently in one pot. Simple extraction or precipitation of 28 from the reaction mixture followed by recrystallization either from ethanol or other appropriate solvents can furnish compound 28 in high yield and purity without any preliminary chromatographic cleaning.

Scheme 6

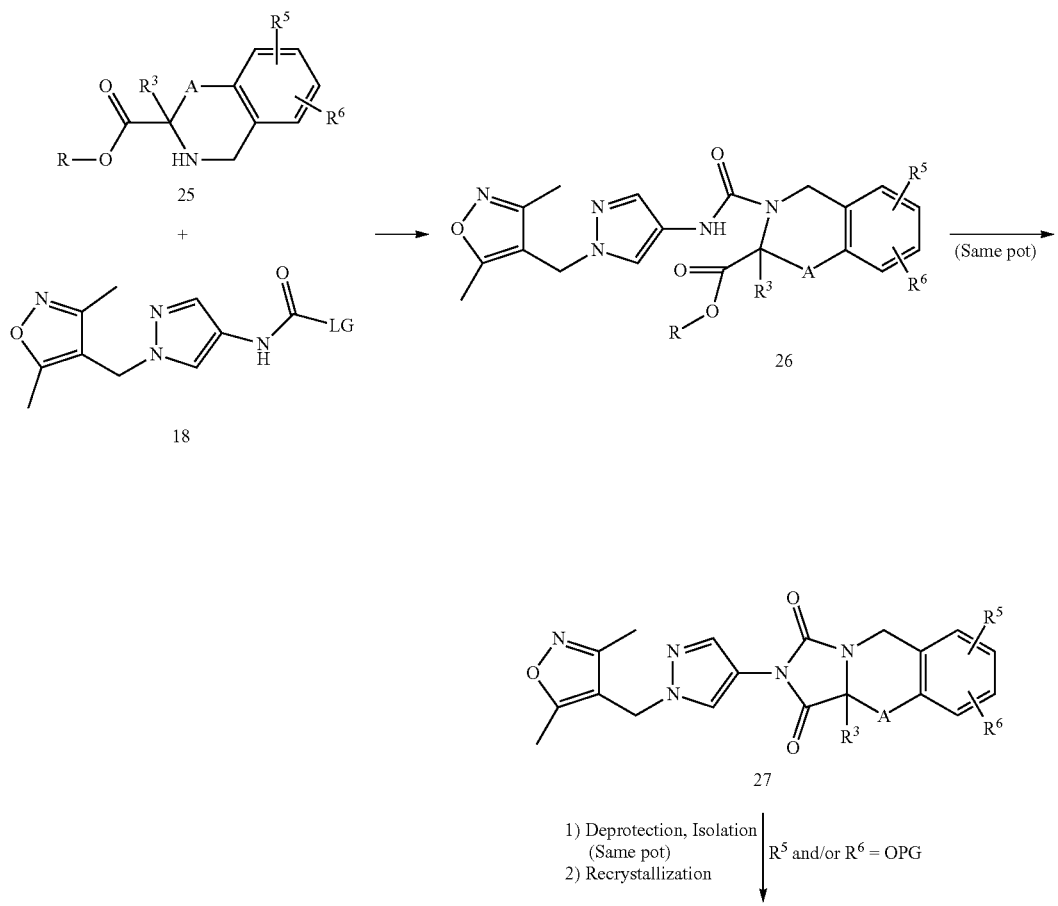

-continued

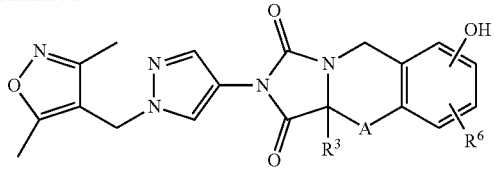

28

R = H, Alkyl, Heteroalkyl, Aryl, or Heteroaryl
$R^3$ = H, Alkyl, Heteroalkyl, Aryl, or Heteroaryl
$R^5$ = H, Alkyl, Heteroalkyl, OH, OPG
$R^6$ = H, Alkyl, Heteroalkyl, OH, OPG
A = $(CH_2)_m$ with m = 0,1
LG = imidazolyl, O-alkyl, O-aryl, O-heteroalkyl or O-heteroaryl
PG = any protecting group The novel process described herein is shown in FIGS. 2, 3, 4, and 5. This process allows for large scale synthesis of substituted 1-benzyl-3-(1-(isoxazol-4-ylmethyl)-1H-pyrazol-4-yl)imidazolidine-2,4-diones by avoiding the use of hazardous hydrazine as well as the hazardous Curtius rearrangement of intermediate acyl azide 9 and 9'a. In addition, this method use cheaper building blocks and improve the overall yield. The steps of this process include: 1) Formation of N-benzylglycine ester IIIb, 4a, 25a, or IIIc from 3-hydroxybenzaldehyde VIIb or 1, (S)-7-hydroxy-1,2,3,4-tetrahydroisoquinoline-3-carboxylic acid, or other corresponding amino acid, 2) Synthesis of Intermediate II or 18a via the aminopyrazole V or 16a, 3) One pot generation of Ie, Ic, If, or Ig starting from N-benzylglycine ester IIIb, 4a, 25a, or IIIc and compound II or 18a via intermediate 19a, 19b, 26a, or 19c and, subsequently, the intermediate hydantoin 11a, 11b, 27a, or 11c, 5) Recrystallization to afford pure Ie, Ic, If, or Ig.

Compounds synthesized according to the invention can be used for modulating, e.g., reducing or alleviating, a bitter taste. The present compounds can reduce or alleviate the bitter taste in a composition, such as coffee, coffee-flavored product, or a composition containing a whey protein, by contacting the present compounds with a composition to form a modified composition. In general, the compounds of the present invention are provided in compositions, such as, e.g., an ingestible composition. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products, and other personal care products that have bitter taste.

The ingestible composition also includes pharmaceutical, medicinal or comestible composition, or alternatively in a formulation, e.g., a pharmaceutical or medicinal formulation or a food or beverage product or formulation.

These compounds and their salts, should preferably be comestibly acceptable, i.e. deemed suitable for consumption in food or drink from the perspective of giving unmodified comestible compositions an improved and/or reduced/alleviated bitter taste, and would not be significantly toxic or causes unpleasant or undesirable pharmacological or toxicological effects on an animal or human at the typically low concentrations they are employed as flavoring agents for the comestible compositions.

The typical method of demonstrating that a flavorant compound is comestibly acceptable is to have the compound tested and/or evaluated by an Expert Panel of the Flavor and Extract Manufacturers Association and declared as to be "Generally Recognized as Safe" ("GRAS"). The FEMA/GRAS evaluation process for flavorant compounds is complex but well known to those of ordinary skill in the food product preparation arts, as is discussed by Smith, et al. in an article entitled "GRAS Flavoring Substances 21," Food Technology, 57(5):46-59 (2003), the entire contents of which are hereby incorporated herein by reference.

The present compounds can also be provided, individually or in combination, with any ingestible composition known or later discovered. For example, the ingestible composition can be a comestible composition or noncomestible composition. By "comestible composition", it is meant any composition that can be consumed as food by humans or animals, including solids, gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical composition, which refers to a noncomestible composition intended to be used by humans or animals for therapeutic purposes. By "animal", it includes any non-human animal, such as, for example, farm animals and pets.

In one embodiment, the compound is added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products and other personal care products that have a bitter taste.

In general, over the counter (OTC) product and oral hygiene product generally refer to product for household and/or personal use which may be sold without a prescription and/or without a visit to a medical professional. Examples of the OTC products include, but are not limited to Vitamins and dietary supplements; Topical analgesics and/or anaesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anaesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene product include, but are not limited to mouth cleaning strips, toothpaste, toothbrushes, mouthwashes/dental rinses, denture care, mouth fresheners at-home teeth whiteners and dental floss.

In another embodiment, the present compounds can be added to food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In another embodiment, the present compounds can be added to compositions comprising vegetable and/or non-vegetable proteins. As used herein, the term "non-vegetable protein(s)" means any protein(s), with the exception of vegetable proteins.

Examples of non-vegetable proteins include, but are not limited to proteins derived from milk (e.g., whey proteins, isolates and other dairy hydrolysates such as milk casein hydrolysates). As used herein, the term "vegetable proteins" means any plant and vegetable protein(s) including, without limitation, proteins from grains (e.g., wheat, corn, barley, oats, rye, millet, and buckwheat); proteins from nuts (e.g., walnuts, cashews, almonds, pecans); proteins from seeds (e.g., sunflower, pumpkin, hemp, and flax); proteins from legumes (e.g., beans, lentils, and garbanzos (chickpeas)); and proteins from rice and pea isolates.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh, instant, and combined coffee; tea, such as black, green, white, oolong, and flavored tea; and other hot drinks including flavor-, malt- or plant-based powders, granules, blocks or tablets mixed with milk or water.

The Snack Food category generally refers to any food that can be a light informal meal including, but not limited to, snacks and snack bars. Examples of snack food include, but are not limited to fruit snacks, chips/crisps, extruded snacks, tortilla/corn chips, popcorn, pretzels, nuts and other snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products. The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or bean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, -based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, beverages or solid or liquid concentrate compositions for preparing food and beverages, so as to reduce or alleviate the bitter taste in the food and beverages.

The concentration of the present compound needed to modulate or reduce the bitter flavor of the ingestible composition will of course depend on many variables, including the specific type of the ingestible composition and its various other ingredients, the natural genetic variability and individual preferences and health conditions of various human beings tasting the compositions, and the subjective effect of the particular compound on the taste of such chemosensory compounds.

The present compounds may be used in pharmaceutical compositions as a taste modulator, such as a bitter taste blocker. In other words, the present compounds can be used to modulate the flavor or taste of pharmaceutical compositions. In one embodiment, the pharmaceutical compositions are administered to a patient via the oral route in a dosage form of solid, semi-solid, liquid, or mixtures thereof.

In pharmaceutical compositions, the present compound can be mixed with other ingredients including the therapeutically active ingredient and pharmaceutically acceptable vehicles. One example of a pharmaceutically acceptable vehicle is water. Saline solutions and aqueous dextrose and glycerol solutions can also be employed as liquid vehicles.

Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the present invention may be manufactured by means of conventional mixing, dissolving, granulating, dragée-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen. In one embodiment, the pharmaceutical composition is a herbal composition, such as the traditional Chinese medicine (TCM).

The present pharmaceutical compositions can take the form of solutions, suspensions, emulsion, tablets, pills, pellets, capsules, capsules containing liquids, powders, sustained-release formulations, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, 20$^{th}$ Edition, 2000).

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

For oral liquid preparations such as, for example, suspensions, elixirs and solutions, suitable carriers, excipients or diluents include water, saline, alkyleneglycols {e.g., propylene glycol), polyalkylene glycols {e.g., polyethylene glycol) oils, alcohols, slightly acidic buffers between pH 4 and pH 6 {e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

Typically at least a bitter flavor/taste modulating amount or a bitter flavor/taste enhancing amount of one or more of the present compound will be added to the ingestible composition so that the bitter flavor modified ingestible composition has a reduced bitter taste as compared to the ingestible composition prepared without the compounds of the present invention, as judged by human beings or animals in general, or in the case of formulations testing, as judged by a majority of a panel of at least eight human taste testers, via procedures commonly known in the field. In one embodiment, for modulating, reducing or alleviating, the bitter taste or other taste properties of other natural or synthetic tastants, and compositions made therefrom, a broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

The present invention is further illustrated by the examples below.

EXAMPLES

The following examples are provided to illustrate embodiments of the present invention but are by no means intended to limit its scope.

Unless otherwise noted, reagents and solvents were used as received from commercial suppliers. Proton nuclear magnetic resonance (NMR) spectra were obtained on Bruker spectrometers at 400 MHz. Spectra are given in ppm (δ) and coupling constants, J, are reported in Hertz. Tetramethylsilane (TMS) was used an internal standard. LC-MS was performed using an Agilent 1100 Series 1956xLC/MS model with mixed mode source. The MSD was in SCAN mode and the UV set to 230 nm. The injection volume per injection was 2 microliters. Solvent A is water+0.05% TFA and solvent B is 100% acetonitrile. The gradient described in Time (min)/% B/Flow was 0.00/10/2.500, 0.70/100/2.500, 1.05/100/4.500, 1.70/100/4.500, and 1.75/10/2.500.

Example 1—Preparation of 3-((tetrahydro-2H-pyran-2-yl)oxy)benzaldehyde (2a)

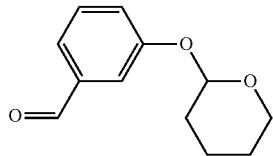 [SMILES: O=Cc1cccc(OC2CCCCO2)c1]

3-Hydroxybenzaldehyde (1) (12.00 g, 98.26 mmol) and 3,4-dihydro-2H-pyran (13.00 g, 154.50 mmol) in anhydrous DCM (250 mL) were treated with p-toluenesulfonic acid (PTSA) (1.00 g) and while stirring, pyridine (2 mL) was added dropwise. After addition was completed the mixture was stirred at RT for 24 h. The crude mixture was washed three times with water and three times with 2N NaOH. The mixture was then washed with brine, dried over MgSO$_4$, filtered and dried under vacuum to give compound (2a) as yellow oil (16.62 g, 80.60 mmol, 82%) that was used in the next step without further purification. $^1$H NMR (DMSO-d$_6$, 400 MHz): δ 1.27-1.97 (m, 6H), 3.48-3.60 (m, 1H), 3.65-3.77 (m, 1H), 5.56 (br. t, J=3.2 Hz, 1H), 7.30-7.36 (m, 1H), 7.48-7.55 (m, 2H), 9.95 (s, 1H).

Example 2—Preparation of ethyl 2-((((tetrahydro-2H-pyran-2-yl)oxy)benzyl)amino)acetate (4a)

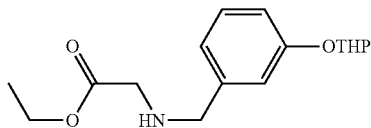

3-((Tetrahydro-2H-pyran-2-yl)oxy)benzaldehyde (2a) (16.00 g, 77.60 mmol) in anhydrous ethanol (250 mL) was treated with ethyl 2-aminoacetate hydrochloride (3a) (11.40 g, 81.50 mmol) and Et$_3$N (8.29 g, 11.43 mL, 82.00 mmol). The mixture was stirred at RT for 2 h and treated portionwise (~4 min) with NaBH$_4$ (6.00 g). After stirring for 1 h, the reaction was treated portionwise (~4 min) with more NaBH$_4$ (5.74 g) for a total of (11.74 g, 310.32 mmol, 4 equiv.). The mixture was stirred at RT for 3 h and volatile materials were removed under vacuum at ~45° C. The residue was treated with water (200 mL) and EtOAc (300 mL). The phases were separated and the aqueous layer was extracted with EtOAc (2×100 mL). The combined organic extract was washed with brine, dried over sodium sulfate and concentrated to give an oily residue that was purified on silica gel column to yield ethyl 2-((3-((tetrahydro-2H-pyran-2-yl)oxy)benzyl)amino) acetate (4a) as a yellow oil (21.9 g, 74.65 mmol, 96%). $^1$H NMR (DMSO-d6, 400 MHz): δ 1.19 (t, J=7.2 Hz, 3H), 1.15-1.95 (m, 6H), 2.42 (br. s, 1H), 3.28 (br. s, 2H), 3.45-3.58 (m, 1H), 3.67 (br. s, 2H), 3.71-3.80 (m, 1H), 4.09 (q, J=7.2 Hz, 2H), 5.44 (br. t, J=3.2 Hz, 1H), 6.85-6.94 (m, 2H), 6.95-6.99 (m, 1H), 7.21 (pseudo t, J=8.0 Hz, 1H). LC/MS; [M+H] 294.10.

Example 3—Preparation of 3,5-dimethyl-4-((4-nitro-1H-pyrazol-1-yl)methyl)isoxazole (14)

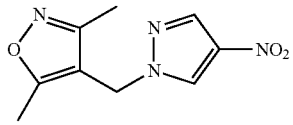 [SMILES: Cc1noc(C)c1Cn1cc([N+](=O)[O-])cn1]

4-Nitro-1H-pyrazole (13) (19.42 g, 171.72 mmol) and 4-(chloromethyl)-3,5-dimethylisoxazole (6a) (25.00 g, 171.72 mmol) in acetone (300 mL) were treated with K$_2$CO$_3$ (26.11 g, 188.92 mmol). The mixture was stirred for 4 hours at 85° C. Upon completion the mixture was cooled down to room temperature, filtered, concentrated and diluted with ethyl acetate (500 mL). The organic layer was wash three times with water (500 mL), dried over Na$_2$SO$_4$, filtered, and concentrated. The crude product was recrystallized from ethyl acetate and hexanes to furnish a solid that was filtered and washed with hexanes. The solid product was dried on high vacuum to furnish 3,5-dimethyl-4-((4-nitro-1H-pyrazol-1-yl)methyl)isoxazole (14) (34.30 g, 154.37 mmol, 90%). $^1$H NMR (DMSO-d$_6$, 400 MHz): δ 2.18 (s, 3H), 2.44 (s, 3H), 5.24 (s, 2H), 8.27 (s, 1H), 8.99 (s, 1H). LC/MS; [M+H] 223.10.

Example 4—Preparation of 1-((3,5-dimethylisoxazol-4-yl)methyl)-1H-pyrazol-4-amine Hydrochloride (16a)

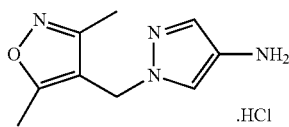

3,5-Dimethyl-4-((4-nitro-1H-pyrazol-1-yl)methyl)isoxazole (14) (5.00 g, 22.50 mmol) in anhydrous MeOH (100 mL) was treated with 10% Pd/C (100 mg, 0.42 mol % of Pd) and the mixture was purged with N$_2$. Triethylsilane (Et$_3$SiH, 25 mL, 18.20 g, 171.24 mmol, 7.61 equiv.) was charged to an addition funnel equipped with a lightly filled N$_2$ balloon and added dropwise to the reaction mixture without used of a cooling bath but while making sure that the temperature stays below 45° C. Bubbling of the reaction mixture was observed. After addition of Et$_3$SiH was completed, stirring continued for about 1 h 45 min and the mixture was cooled to 0° C. At this point, bubbling has ceased. A solution of HCl (1.25 M in MeOH, 45 mL, 2.5 equiv) was charged to the addition funnel and added dropwise at 0° C. to the reaction mixture. After the addition was completed, stirring continued for 2 h at the same temperature. The reaction was then filtered through celite. The methanolic filtrate (~200 mL) was concentrated to about 50 mL of residual mixture and diluted with anhydrous toluene (150 mL). The mixture was heated to 50° C. and stirred for ~30 min. After cooling down to RT, the precipitate was filtered, washed with toluene and subsequently with MTBE. The solid was collected and dried under vacuum to afford 4.97 g (21.69 mmol, 96.4%) of the desired compound (16a) as HCl salt. $^1$H NMR (DMSO-d$_6$, 400 MHz): δ 2.14 (s, 3H), 2.41 (s, 3H), 5.19 (s, 2H), 7.54 (d, j=0.8 Hz, 1H), 8.05 (s, 1H), 10.23 (s, 3H).

Example 5—Preparation of N-(1-((3,5-dimethyl-isoxazol-4-yl)methyl)-1H-pyrazol-4-yl)-1H-imidazole-1-carboxamide (18a)

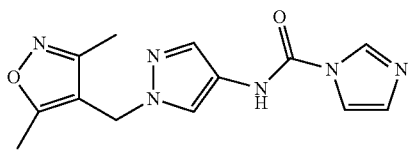 [SMILES: Cc1noc(C)c1Cn1cc(NC(=O)n2ccnc2)cn1]

1-((3,5-Dimethylisoxazol-4-yl)methyl)-1H-pyrazol-4-amine hydrochloride (16a) (4.50 g, 19.68 mmol) in water (10 mL) was treated with 5N NaOH solution until pH 7.5. The solution was then extracted with EtOAc (3×200 mL), dried over sodium sulfate and filtered. The filtrate was dried under vacuum and the residue was evaporated three times from anhydrous ACN and, finally, dried overnight under vacuum to give 3.16 g (16.44 mmol, 84%) of the free base as a light brown material. This material (3.10 g, 16.13 mmol) was dissolved in anhydrous ACN (60 mL), cooled to 0° C. and treated in small portions over ~1 min with CDI (3.93 g, 24.19 mmol, newly open bottle is preferred). After the addition was completed, the cooling bath was removed. The solution became homogeneous but a solid suspension was formed less than 10 min after removal of the cooling bath. The reaction was stirred, vigorously, overnight at RT, cooled to 10° C., filtered and the solid was washed with precooled anhydrous ACN. The solid was collected and dried under vacuum to yield compound (18a) (4.25 g, 14.85 mmol, 92%) as a white powder. The combined yield for the free basing and subsequent reaction with CDI is 78%. $^1$H NMR (DMSO-ds, 400 MHz): δ 2.15 (s, 3H), 2.41 (s, 3H), 5.17 (s, 2H), 7.08 (dd, J=0.8, 1.6 Hz, 1H), 7.56 (d, J=0.4 Hz, 1H), 7.75 (pseudo t, J=1.6 Hz, 1H), 8.00 (d, J=0.8 Hz, 1H), 8.32 (pseudo t, J=1.2 Hz, 1H), 10.46 (s, 1H).

Example 6—Preparation of 3-(1-((3,5-dimethylisoxazol-4-yl)methyl)-1H-pyrazol-4-yl)-1-(3-hydroxybenzyl)imidazolidine-2,4-dione (Ic)

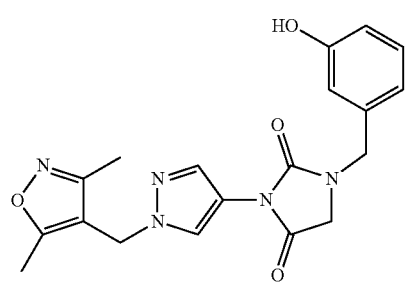 [SMILES: Cc1noc(C)c1Cn1cc(N2C(=O)CN(Cc3cccc(O)c3)C2=O)cn1]

A mixture of N-(1-((3,5-dimethylisoxazol-4-yl)methyl)-1H-pyrazol-4-yl)-1H-imidazole-1-carboxamide (18a) (4.20 g, 14.67 mmol, 1 equiv.) and ethyl 2-((3-((tetrahydro-2H-pyran-2-yl)oxy)benzyl)amino)acetate (4a) (4.52 g, 15.40 mmol, 1.05 equiv.) in anhydrous DMF (30 mL) was stirred at RT until LC-MS indicated a complete consumption of compound-18a and formation of the urea intermediate (~4 h). Typically, the LC-MS sample was dissolved in MeOH and unreacted compound-18a could be observed either directly or as methyl-carbamate derivative. The reaction was treated with ammonia (7N solution in MeOH, 1 mL) and the septum caped reaction vessel was stirred at RT until LC-MS indicated complete cyclisation of urea intermediate to the protected hydantoin (~1 h). The reaction product was subsequently treated dropwise with concentrated hydrochloric acid (8 mL, 5 equiv.) and stirred until complete disappearance of the hydantoin intermediate to form the desired compound (3h). The reaction was diluted with water (100 mL) and extracted with EtOAc. The organic extract was washed with water, brine, and dried over sodium sulfate. After filtration, the filtrate was concentrated under vacuum at 40° C. to give the residual solid that was recrystallized from ethanol at 4° C. overnight to give 3-(1-((3,5-dimethylisoxazol-4-yl)methyl)-1H-pyrazol-4-yl)-1-(3-hydroxybenzyl)imidazolidine-2,4-dione (Ic) as a white solid (4.74 g, 12.43 mmol, 85%). $^1$H NMR (DMSO-ds, 400 MHz): δ 2.15 (s, 3H), 2.41 (s, 3H), 3.99 (s, 2H), 4.45 (s, 2H), 5.21 (s, 2H), 6.65-6.76 (m, 3H), 7.1-7.18 (m, 1H), 7.80 (d, J=0.8 Hz, 1H), 8.19 (d, J=0.8 Hz, 1H), 9.44 (s, 1H). LC/MS: [M+H] 382.1.

Example 7—Preparation of (S)-methyl 7-hydroxy-1,2,3,4-tetrahydroisoquinoline-3-carboxylate Hydrochloride (25a)

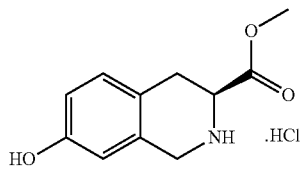

Thionyl chloride (1 mL, 1.64 g, 13.78 mmol) was added dropwise under nitrogen atmosphere at −15 C to anhydrous methanol (10 mL). After stirring for about 10 min at −15 C, (S)-7-hydroxy-1,2,3,4-tetrahydroisoquinoline-3-carboxylic acid (1.00 g, 5.17 mmol) was added and the mixture was warmed up slowly to reflux and stirred for 1 h. After cooling down to room temperature, the reaction was stirred overnight and dried under vacuum to give the desired compound (25a) as a white powder in quantitative yield. $^1$H NMR (DMSO, 400 MHz): δ 3.02 (dd, J=11.2, 16.4 Hz, 1H), 3.17 (dd, J=5.2, 16.8 Hz, 1H), 3.80 (s, 3H), 4.24 (pseudo t, J=16.8, 18.4 Hz, 2H), 4.49 (dd, J=5.2, 11.2, Hz, 1H), 6.63 (d, J=2.4 Hz, 1H), 6.71 (dd, J=2.8, 8.4 Hz, 1H), 7.04 (d, J=8.0 Hz, 1H), 9.59 (s, 1H), 10.03 (br. s, 1H). LC/MS: [M+H−Cl] 208.1.

Example 8—Preparation of (S)-2-(1-((3,5-dimethyl-isoxazol-4-yl)methyl)-1H-pyrazol-4-yl)-7-hydroxy-10,10a-dihydroimidazo[1,5-b]isoquinoline-1,3(2H,5H)-dione (If)

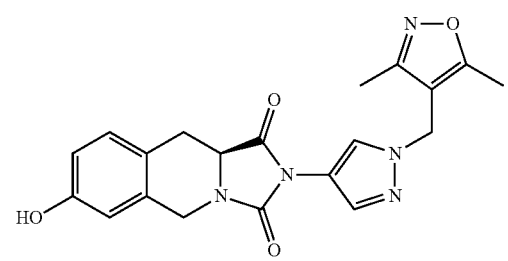 [SMILES: Cc1noc(C)c1Cn1cc(N2C(=O)[C@@H]3Cc4ccc(O)cc4CN3C2=O)cn1]

N-(1-((3,5-dimethylisoxazol-4-yl)methyl)-1H-pyrazol-4-yl)-1H-imidazole-1-carboxamide (18a) (117.5 mg, 410.36 umol, 1 equiv.) was added at 0° C. to a solution of(S)-methyl 7-hydroxy-1,2,3,4-tetrahydroisoquinoline-3-carboxylate hydrochloride (25a) (105 mg, 430.88 umol, 1.05 equiv.) and N-ethyl-N-isopropylpropan-2-amine (DIEA) (192 uL, 985.02 umol, 2.4 equiv.) in anhydrous DMF (1 mL) and the mixture was stirred at 0° C. for 90 min. The reaction was slowly warmed up to room temperature, stirred for another 90 min and diluted with water (1 mL). The mixture was acidified to pH 2 with a 2M aqueous HCl solution. Water (10 mL) was added and the suspension was stirred overnight. The precipitate was filtered, washed with water and dried under reduced pressure to give (S)-2-(1-((3,5-dimethylisoxazol-4-yl)methyl)-1H-pyrazol-4-yl)-7-hydroxy-10,10a-dihydroimidazo[1,5-b]isoquinoline-1,3(2H,5H)-dione (If) as a whitish powder (159 mg, 404.2 umol, 98.5%). $^1$H NMR (DMSO, 400 MHz): δ 2.15 (s, 3H), 2.42 (s, 3H), 2.85 (dd, J=11.6, 15.2 Hz, 1H), 3.07 (dd, J=4.8, 15.2 Hz, 1H), 4.25-4.42 (m, 2H), 4.79 (d, J=16.8 Hz, 1H), 5.21 (s, 2H), 6.59-6.71 (m, 2H), 7.06 (d, J=8.0 Hz, 1H), 7.81 (s, 1H), 8.20 (s, 1H), 9.40 (s, 1H), LC/MS: [M+H] 394.1.

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (II):

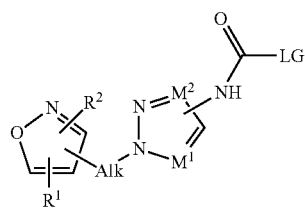

(II)

wherein Alk is an alkyl group;

M$^1$ is N or CR$^8$, wherein R$^8$ is H or substituted or unsubstituted alkyl;

M$^2$ is N or CR$^9$, wherein R$^9$ is H or substituted or unsubstituted alkyl;

R$^1$ is selected from the group consisting of H, substituted or unsubstituted alkyl, substituted or unsubstituted heteroalkyl, substituted or unsubstituted alkoxy, and substituted or unsubstituted alkylaryl;

R$^2$ is selected from the group consisting of H, substituted or unsubstituted alkyl, substituted or unsubstituted heteroalkyl, substituted or unsubstituted alkoxy, and substituted or unsubstituted alkylaryl; and LG is selected from the group consisting of imidazolyl, O-alkyl, O-aryl, O-heteroaryl, O-alkyaryl, O-halogenated alkyl, and halo, or an oxide thereof, a salt thereof, or a solvate thereof.

2. A compound according to claim 1, wherein the compound of formula (II) is represented by formula (IIa):

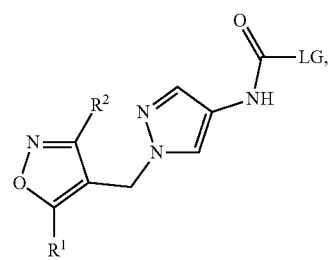

(IIa)

wherein LG, R$^1$, and R$^2$ are the same as defined in claim 1.

3. A compound according to claim 1 which is selected from the group consisting of

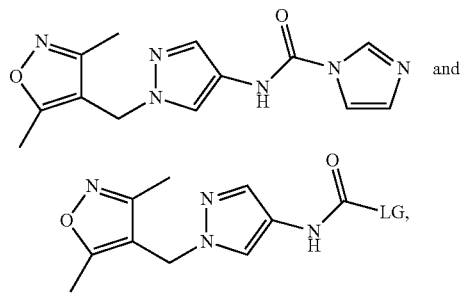

and wherein

LG is selected from the group consisting of O-alkyl, O-aryl, O-heteroalkyl O-heteroaryl, O-alkyaryl, O-halogenated alkyl, and halo, or an oxide, salt, or solvate thereof.

4. A composition comprising a compound synthesized according to claim 1.

5. The composition of claim 4, wherein the compound is a compound of formula (IIa) or a salt, solvate, or an obvious chemical equivalent thereof.

6. An oxide, a salt, or a solvate of a compound according to claim 1 suitable for animal or human consumption.

7. The composition of claim 4, wherein the compound is selected from the group consisting of
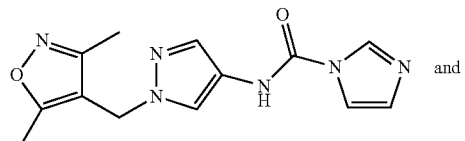
and
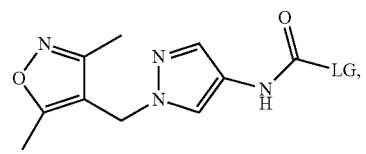
or a salt, solvate, or an obvious chemical equivalent thereof.
* * * * *